United States Patent [19]

Antich et al.

[11] Patent Number: 5,038,787
[45] Date of Patent: Aug. 13, 1991

[54] METHOD AND APPARATUS FOR ANALYZING MATERIAL PROPERTIES USING REFLECTED ULTRASOUND

[75] Inventors: Pietro P. Antich; James E. Dowdey; Robert C. Murry, Jr., all of Dallas, Tex.

[73] Assignee: The Board of Regents, The University of Texas System, Austin, Tex.

[21] Appl. No.: 230,845

[22] Filed: Aug. 10, 1988

[51] Int. Cl.$^5$ .............................................. A61B 8/00
[52] U.S. Cl. .......................... 128/660.01; 128/660.08; 73/602
[58] Field of Search ...................... 128/660.01, 660.06, 128/660.08, 661.03; 73/599, 602, 624

[56] References Cited

U.S. PATENT DOCUMENTS

| | | | |
|---|---|---|---|
| 4,098,129 | 7/1978 | Deblaere et al. | 73/624 X |
| 4,682,497 | 7/1987 | Sasaki | 73/602 |

OTHER PUBLICATIONS

J. F. Whiting, Ultrasonic Critical Angle Reflection Goniometer for in Vivo Bone, *Ultrasound in Medicine,* Eds. D. White and R. E. Brown (Pleum: New York, 1977).

W. G. Mayer, Determination of Ultrasonic Velocities by Measurement of Angles of Total Reflection, *Journal of Accoustical Society of America,* (Oct. 1960, vol. 32, No. 10).

W. G. Mayer, Reflection and Refraction of Mechanical Waves at Solid-Liquid Boundaries, *Journal of Applied Physics,* (Apr. 1963, vol. 34, No. 4).

S. Lees, Data Reduction from Critical Angle Reflection Measurements, *Ultrasonics, (Sep. 1975).*

L. S. Fountain, Experimental Evaluation of the Total-Reflection Method of Determining Ultrasonic Velocity, *Journal of Acoustical Society of America,* (Jan. 1967).

W. G. Mayer, Energy Partition of Ultrasonic Waves at Flat Boundaries, *Ultrasonics,* (Apr.-Jun., 1965).

J. C. Couchman, B. G. W. Yee and F. H. Chang, Energy Partitioning of Ultrasonic Waves Beyond the Critical Angle at Flat Boundaries, *Ultrasonics, Mar. 1974).*

F. R. Rollins, Jr., Ultrasonic Examination of Liquid-Solid Boundaries Using a Right Angle Reflector Technique, *Journal of the Accoustical Society of America,* (Feb. 1968).

S. Lees and F. R. Rollins, Jr., Antisotropy in Hard Dental Tissues, *J. Biomechanics,* (1972, vol. 5, pp. 557-566).

(List continue on next page.)

*Primary Examiner*—Francis Jaworski
*Attorney, Agent, or Firm*—Arnold, White & Durkee

[57] ABSTRACT

A method and apparatus which assesses the mechanical properties of a material by launching an ultrasound signal at the material while varying the angle of incidence and analyzing the amplitude of the ultrasound wave reflected by the material. The method and apparatus correlates extrema (maxima or minima inflection points) in the reflected angle with the angle of incidence of the transmitted signal to identify critical angles of incidence. The velocity of the pressure wave in the material has been found to be a function of a first critical angle corresponding to a first maxima as the angle of incidence is increased in the range 0°-90°. The velocity of the shear wave in the material has been found to be a function of a second critical angle corresponding to a second maxima following the first maxima. Young's modulus of elasticity, Poisson's modulus, and density can be approximated using the velocity of the pressure wave and shear wave for isotropic materials. A third critical angle corresponding to a minima after the first critical angle (reflected amplitude approaching o) has been found particularly useful in conjunction with the first and second critical angles in assessing bone density and in determining whether the second critical point is at a maximum or an inflection point. The extension of the method in which the plane of scattering is rotated around the normal to bone while keeping the point of observation fixed has been found particularly useful in assessing the mechanical properties of anisotropic materials such as cortical bone.

57 Claims, 11 Drawing Sheets

OTHER PUBLICATIONS

W. Weston-Bartholomew, Temperature Consicderations when Evaluating Materials Using the Ultrasonic Goniometer (Critical Angle Reflectometry), *Ultrasonics* (May).

"Ultrasonic Bone Scanning Device", *Biologue, p. 6 (1987-88)*.

Currey, Clinical Orthopedics and Related Research, 21014 231 (Nov.-Dec. 1970).

Abendschein, Clinical Orthopedics and Related Research, 294-301 (Mar.-Apr. 1970).

Greenfield, Ultrasound, 115:163-166 (1971).

Greenfield, Radiation Physics, 138:701-710 (1981).

Craven, Investigative Radiology, 8:72-77 (1973).

Lees, Sonic Properties of Mineralized Tissues, Tissue Characterization with Ultrasound, Chapter 9, pp. 207-226 (1986).

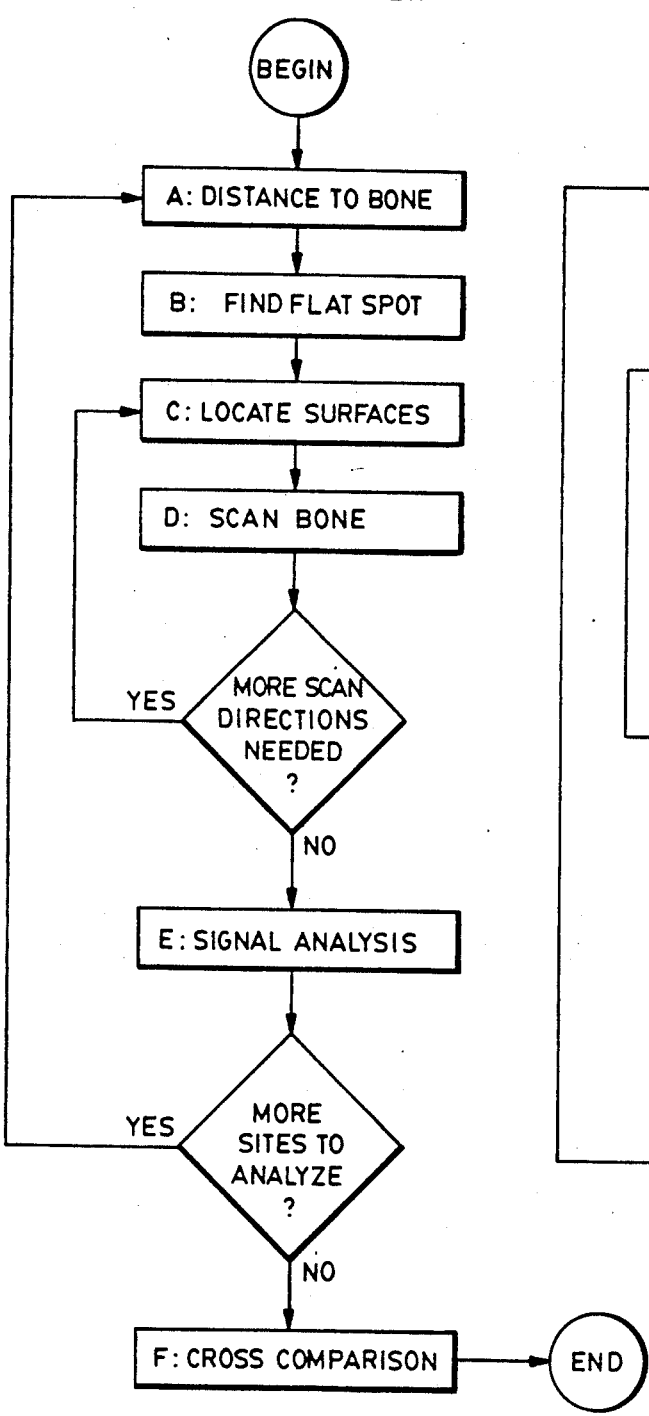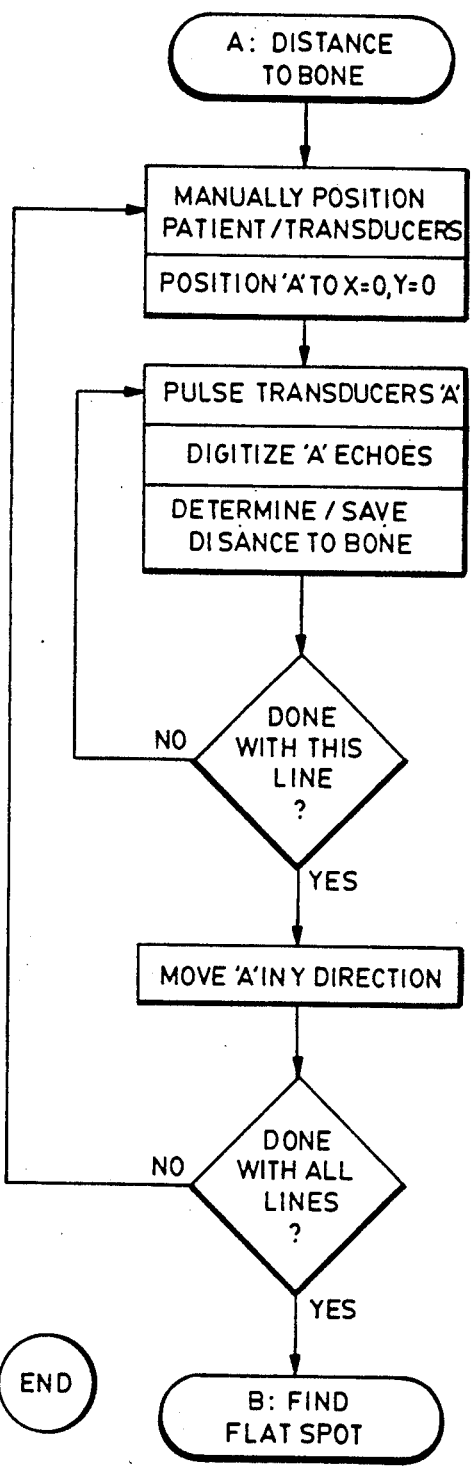

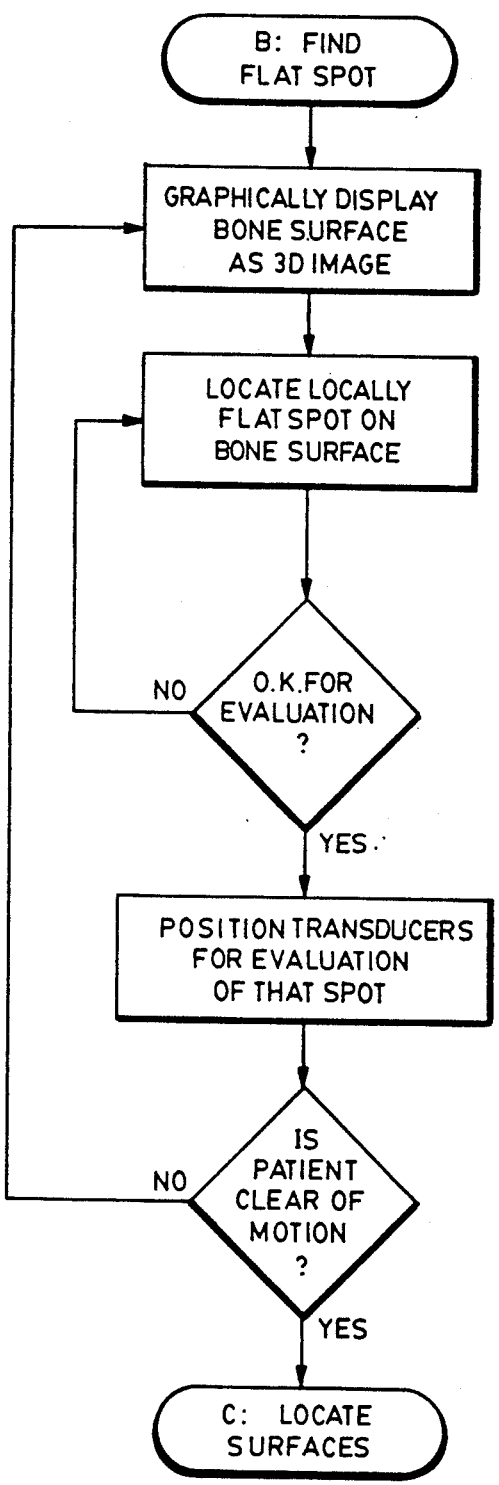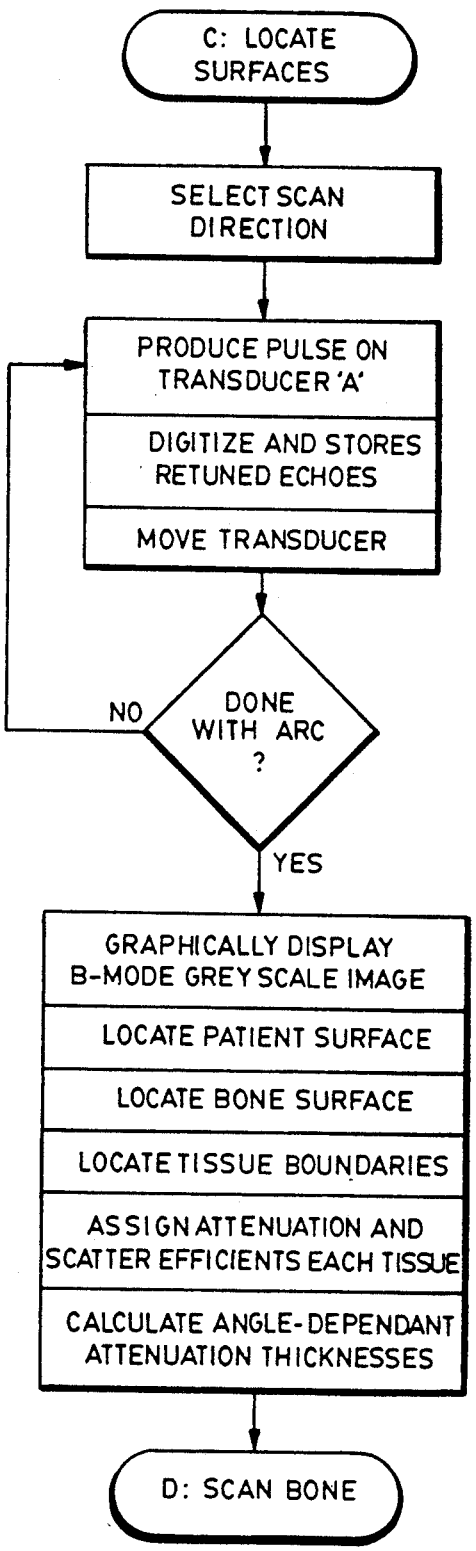

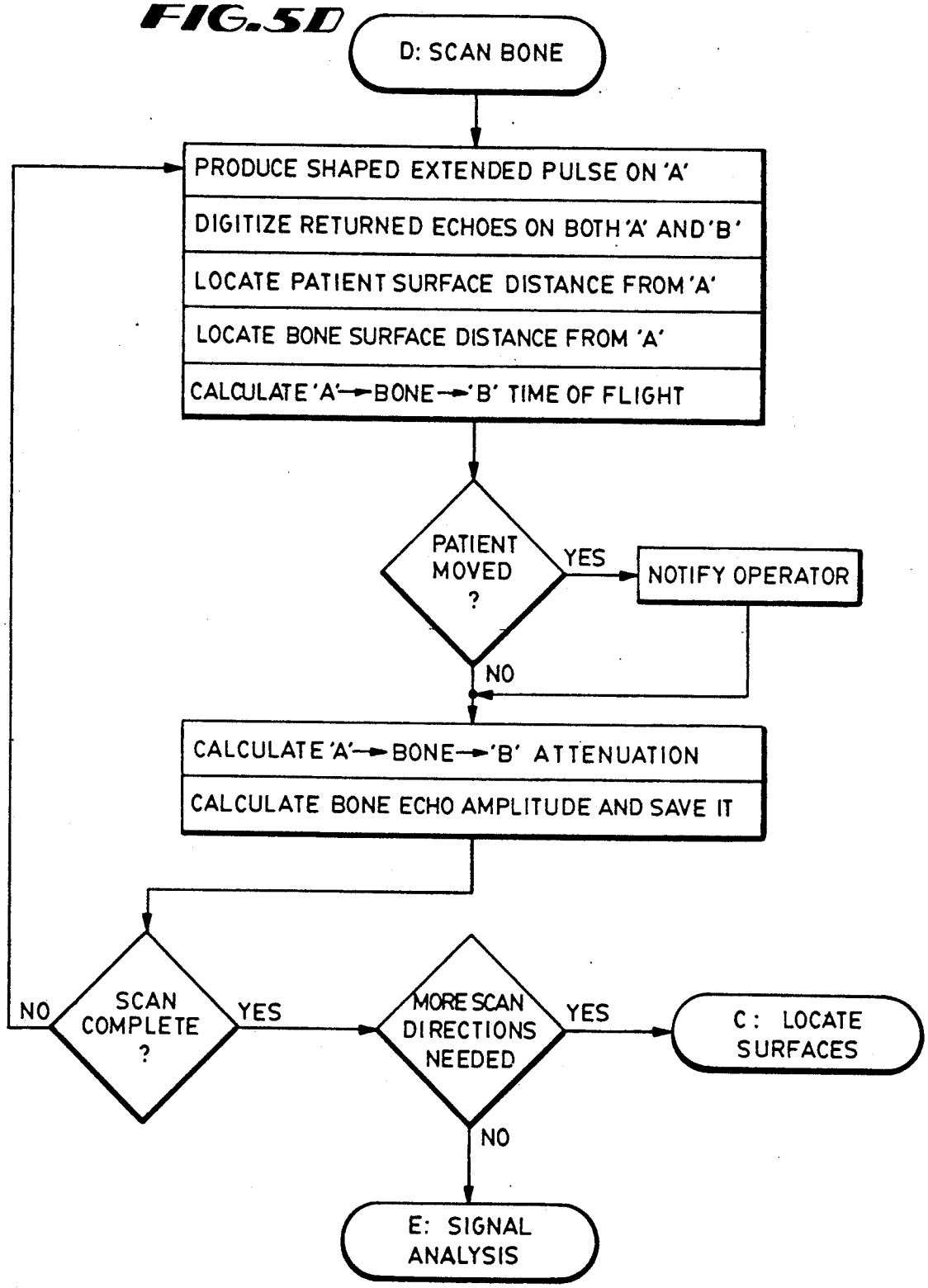

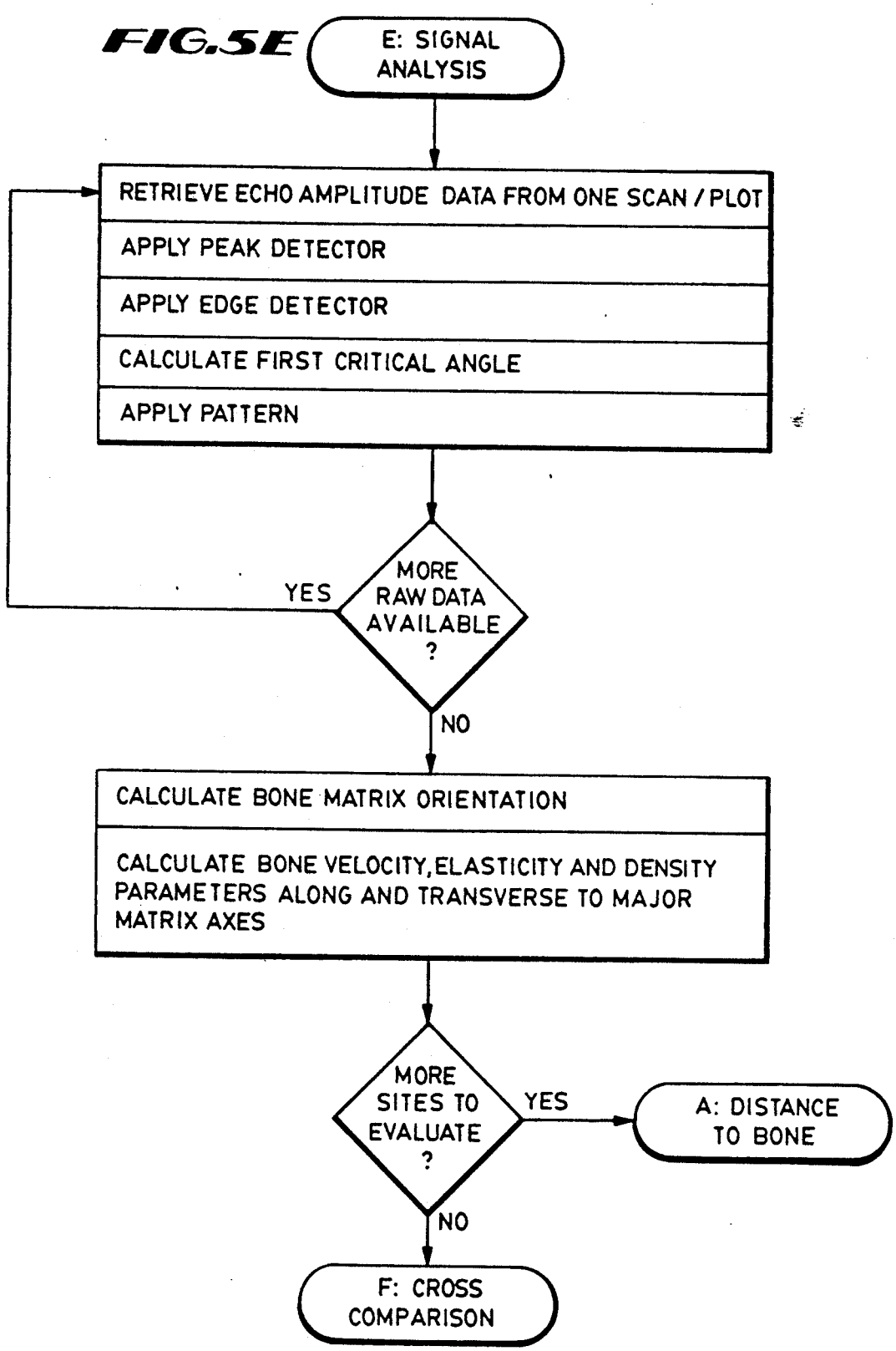

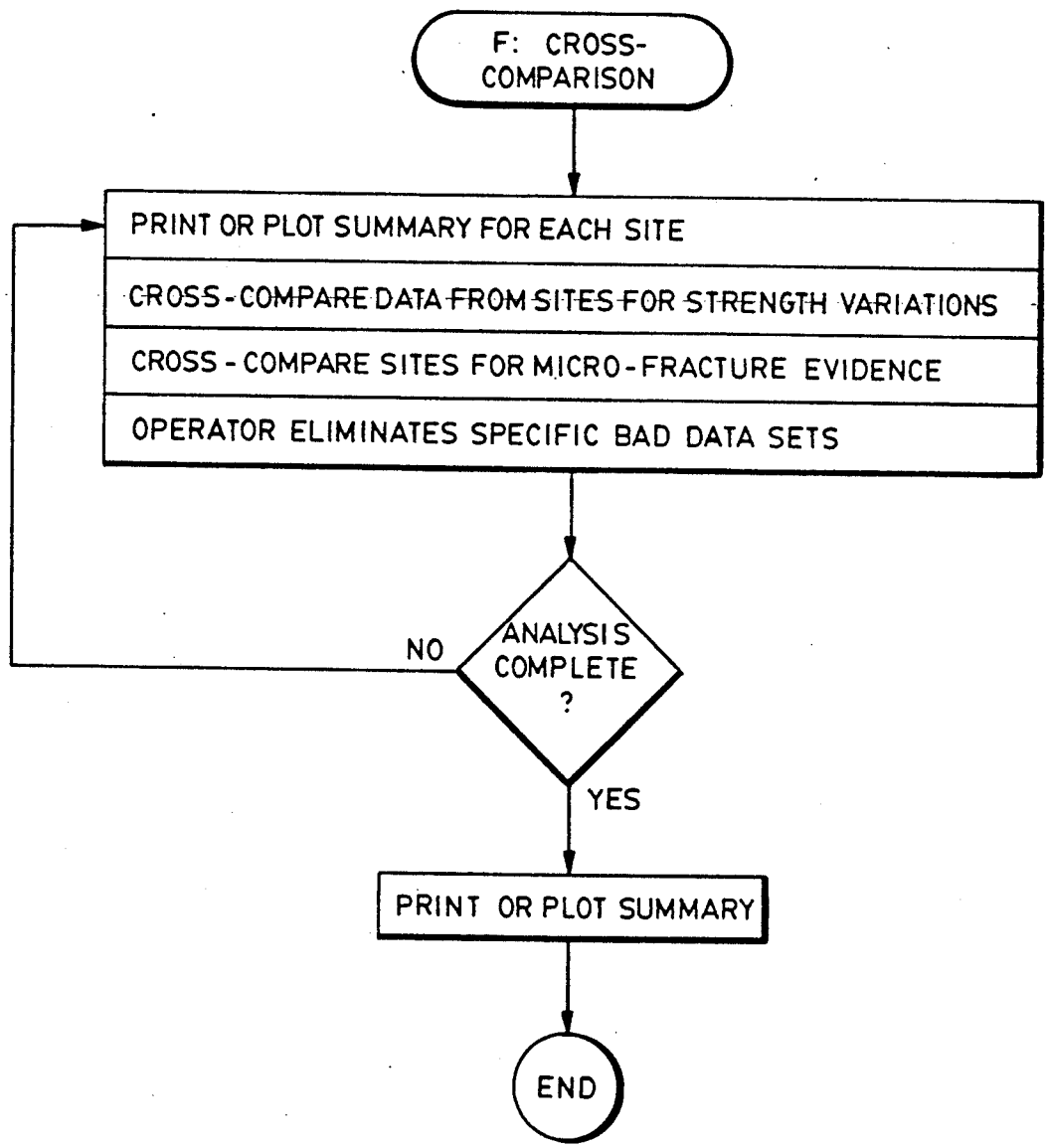

METHOD AND APPARATUS FOR ANALYZING MATERIAL PROPERTIES USING REFLECTED ULTRASOUND

BACKGROUND OF THE INVENTION

1. Field of the Invention

This invention relates to a method and apparatus for investigating the mechanical properties of a material. In particular, the present invention relates to the noninvasive use of ultrasound for assessment of bone mass and strength by analyzing the reflection of ultrasound waves at the soft tissue-bone interface.

2. Outline of Problem

The need for assessing the mechanical properties of a material is found in a wide variety of applications. For example, it is necessary to test the strength of materials in a wide variety of industrial applications. In many applications, destructive testing techniques can be utilized to determine the mechanical properties of a material. In other types of material testing, the material is easily accessible for analysis and nondestructive techniques can be utilized. Further, many materials are homogenous on a macroscopic level, permitting simplified techniques based upon assumptions of the homogeneity.

While many different techniques have been developed for investigating the mechanical properties of materials, many types of materials are not accurately analyzed using conventional techniques. For example, in many medical applications, it is desirable to determine the mechanical properties of the material for proper diagnosis and treatment. In many medical applications, however, the testing is difficult to analyze because destructive testing cannot be used, invasive types of testing are undesirable, and the non-homogenous nature of biological tissue presents unique problems. A good example is the need for accurate measurement of bone mass and bone strength as an indication of resistance to fracture.

The capability to accurately assess resistance to fracture would have great clinical significance in the diagnosis and treatment of numerous medical problems such as osteoporosis. In osteoporosis, bone mass is lost gradually and progressively thus decreasing the mechanical strength of the skeleton until even minimal trauma results in bone fracture. Osteoporosis affects one in three women and one in five men over the age of 60. Over 80% of the one million fractures sustained yearly by women over the age of 50 in the United States is a consequence of osteoporosis. Half of the patients with fractures resulting from osteoporosis never recover normal functions, and 30% progress to premature death, 10% dying within three months because of peri- and post-operative complications. However, treatments exist which alter, delay or reverse the progression of osteoporosis if the disease is accurately diagnosed before fracture occurs. The development of improved treatments would be greatly facilitated by a technique capable of delineating their effectiveness.

Unfortunately, assessment of osteoporosis is difficult. Only a small portion of elderly osteoporotic women and men have whole skeletons demonstrating a discernible degree of osteoporosis. That is, different sites in the skeleton are associated with different degrees of osteoporosis. Further, bones are inherently non-homogeneous making assessment difficult even on a localized basis. Finally, the nature of the disease dictates an accurate, non-invasive technique for diagnosis and assessment.

3. Description of Current Methods

Currently there is no widely accepted accurate method to diagnose and assess bone strength as an indication of resistance to fracture. Indeed, osteoporosis is usually diagnosed only after a fracture occurs. A number of methods have been proposed, however, all of which have a number of problems. Biochemical analysis of bone tissue correlates very poorly with bone strength, because osteoporosis is the result of long term metabolic deficiencies and strong temporal correlation between the disease and biochemical analysis is not clear. Invasive methods such as bone biopsies are usually accurate determinations of bone mechanical properties, but are only accurate at the site of a biopsy. That is, the bone biopsy taken from the region of the iliac crest may give little indication of the extent of osteoporosis of the lumbar vertebrae or femoral neck.

Additionally, there are a number of non-invasive techniques which have been introduced to diagnose and assess the extent of osteoporosis. For example, radiogrammetry has been used to measure the thickness of the cortex, photodensitometry measures the photographic density, and single-photon absorptiometry measures mineral content. While these methods are useful in measuring bone density and bone mineral density in the appendicular skeleton, they are of little value in assessing osteoporosis in the spine or hip. Dual-photon and computed tomography are usable in the spine or hip, but are of limited value in other respects. In dual-photon absorptiometry, only an integrated attenuation is measured, thus cortical and trabecular bone are not independently assessed. Calcification outside the bone of interest, bone shape, and vertebrae compression and deformity can alter the results. Computed tomography (single energy) is biased by marrow fat concentration, but can measure geometric non-homogeneities and in particular, differentiate between cancellous and cortical bone. However, neither dual-photon nor computed tomography can accurately predict the tendency of bone to fracture.

Neutron activation analyses can quantify the presence of calcium in the whole body or at selected sites. The doses involved are typically in the range of 0.3 to 3 rem. However, neutron activation analysis cannot accurately predict the tendency of a bone to fracture and appears to be too expensive for practical use.

Nuclear medicine studies utilize radionuclides having particular skeletal bone affinity and are good indicators of bone turn over in kinetic parameters. Unfortunately, nuclear medicine studies are difficult and must be carried out at frequent intervals for long time periods and nevertheless do not yield a good indication of the tendency of bone fracture.

Several techniques have been proposed to study the mechanical properties of bone directly in vivo. For example, a variety of instruments have been designed which use static or frequency loading of the bone to measure the resonant frequency and impedance as well as measurement of velocity and elastic modulus by ultrasound. U.S. Pat. Nos. 4,361,154 and 4,421,119, Pratt, Jr. are indicative of past uses of ultrasound to analyze bone strength. In such preexisting ultrasound techniques, an ultrasound pulse is launched from the transducer on one side of the bone and received at a transducer on the other side of the bone. The distance between transducers is used to determine the effective velocity of the pulse through the bone and tissue, and the assumed speed of the ultrasound through the soft tissue subtracted to give an apparent velocity of the ultrasound through the bone. However, such an ultrasound technique as described in the Pratt, Jr. patents is not an accurate prediction of the tendency of fracture for a number of reasons.

First, the velocity through the bone is measured indirectly and hence inaccurately, because the technique measures only the time difference and the path of travel is measured by a non-ultrasound method. Second, the measurement of the path of travel is inaccurate because bone is non-homogenous and anisotropic—meaning that the path of travel of the ultrasound is not equal to the distance between the transducers, which is the distance measured. Third, even assuming the time and distance of the path of travel could be accurately measured, the result would yield only a pressure wave velocity through the bone, limiting its usefulness. Because bone is mineralized tissue, ultrasound waves propagating through it are not merely pressure waves as in soft tissue, but have a significant transverse or shear component which must be assessed to adequately investigate the mechanical properties of bone. Finally, the ultrasound signal is strongly attenuated by bone at frequencies of 1 megaHertz, making only low frequency ultrasound usable. Thus, present ultrasound techniques for investigating the mechanical properties of materials such as bone, present inherent difficulties in accurately predicting mechanical properties, such as the likelihood of a bone fracture.

SUMMARY OF THE INVENTION

The present invention represents a major advance in investigating the mechanical properties of materials by analyzing the ultrasound waves reflected by the material surface. The present invention identifies critical angles of reflection and uses such critical angles to evaluate the mechanical properties of a material. The present technique uses non-invasive ultrasound and does not attempt to measure pressure wave velocity through a material directly. Thus, the present invention may find widespread use in a variety of applications for the investigation of the mechanical properties of a material, particularly where the material necessitates a nondestructive, noninvasive technique, even if the material has a nonhomogeneous structure. Because the mechanical properties of bone are difficult to assess, bone is used as a nonlimiting example, it being understood that the methods and apparatus of the present invention may be used with other materials.

The present invention utilizes ultrasound waves launched through the soft tissue at the bone site under investigation. The ultrasound divides into pressure and shear waves propagating in the bone, as well as a reflected wave returning through the soft tissue. The present invention analyzes the reflected wave alone in assessing the mechanical properties of the bone. That is, the present invention varies the angle of incidence of the launched ultrasound and identifies the extrema (maxima, minima) and inflection points of the angular distribution of the reflected amplitude to measure the critical angles of incidence. From these critical angles of incidence the mechanical properties of the bone can be derived—and expressed through the matrix of elasticity. For isotropic materials, the matrix of elasticity reduces to the modulus of elasticity and Poisson's modulus. The elements of the matrix characterize bone with respect to mechanical properties, and hence ultimately bone strength and resistance to fracture at the site.

The present invention is particularly advantageous over current techniques in that it can be applied in vivo noninvasively, avoiding radiation side effects and other deficiencies of current methods. Further, both the pressure and shear wave velocities are obtained giving a more accurate picture of the bone parameters at the site of investigation. Pressure and shear velocities are measured directly from the ultrasound signal alone, with no additional non-ultrasound measurements necessary. The ultrasound measurements occur locally over a selected area, which is typically 1 cm $\times$ 1 cm and can be as small as 0.1 cm by 0.1 cm, minimizing the effects of non-homogeneity at the site under investigation. Importantly, reflected ultrasound signal under analysis propagates only in the soft tissues or other medium surrounding the bone, obviating bone absorption and permitting higher frequencies (greater than 1 megaHertz). Finally, mechanical properties derived from the identification of the critical angles—e.g. Young's modulus of elasticity and Poisson's modulus—are expected to correlate excellently with resistance to fracture.

Broadly speaking, the apparatus of the present invention includes means for transmitting an ultrasound wave towards the surface of the material, means for receiving the ultrasound wave reflected from the surface of the material, and means for varying the angle of incidence of the transmitted ultrasound wave. A signal analyzer means is included and performs the following functions:

(1) it is coupled to the receiving means for determining when the amplitude of the reflected wave (R) is an extrema;

(2) it is coupled to the varying means to determine the angle of incidence ($\phi$) of the transmitted ultrasound wave (I) relative to the material; and (3) is operable to correlate the extrema of the reflected amplitude to said angle of incidence ($\phi$) to determine the one or more critical angles corresponding to said maxima.

As used herein, "extrema" means one or more maximum or minimum amplitudes where the reflected amplitude is a localized maximum or minimum or an inflection point (change of curvature) found over a limited range of angles of incidence. Therefore, one or several "extrema" may be found in the full range of angles of incidence assessed. It is not necessary to quantify the extrema—rather identification of the corresponding critical angles is sufficient.

In a preferred form, transmitting and receiving means each comprise a ultrasound transducer and the varying means includes a stepper mechanism which incrementally steps the transmitting and the receiving transducer through increasing angles of incidence. In the present laboratory embodiment, the transmitting and receiving transducers are simultaneously stepped such that the angle of incidence is equal to the angle of reflection. In another form, an array of ultrasound transducers is provided where a single transducer (or a limited number) is operable as the transmitting means and another transducer (or the remaining bank of transducers) is operable as the receiving means and the varying means electronically steps through matched pairs or groups of receiving and transmitting transducers for varying the angle of incidence. In another preferred form, the bone under investigation is placed in a water tank and the ultrasound directed through the water medium and the soft tissue to the surface of the bone. In an alternative embodiment, a water bag is placed against the ultrasound transducers and is positionable to adjoin the bone under investigation.

In enhanced embodiments, the signal analyzer is operable for measuring (at least approximately) the pressure wave velocity ($V_p$) in the material based upon a first critical angle corresponding to the first maxima encountered as an angle of incidence ($\phi$) increases in the range of 0–90°. In another enhancement, the signal analyzer is operable for measuring the shear wave velocity ($V_s$) in the material based upon a second critical angle identified as corresponding to a second maxima encountered after the first maxima. In a still further enhancement, the signal analyzer is operable to measure the density, Young's modulus of elasticity, and Poisson's modulus based on the pressure and shear velocities ($V_p$), and ($V_s$) and on the identification of a minimum (zero) the amplitude.

Broadly speaking, the method of the present invention includes the steps of directing ultrasound waves (I) towards the surface of the material at an angle of incidence ($\phi$) while the angle of incidence ($\phi$) of the directed waves (I) relative to the surface of the material is varied. Reflected ultrasound waves (R) are received from the surface of the material. The angle of incidence ($\phi$) is varied and one or more critical angles of incidence corresponding to maxima values of the amplitude of the reflected ultrasound waves (R) are determined.

Preferably, the method further includes measuring the velocity of the pressure wave ($V_p$) in the material using an identified first critical angle ($\phi_1$) Preferably, the pressure wave velocity is calculated using the relationship:

$$V_p = \frac{c}{\sin \phi_1},$$

where $\phi_1$ is the first identified critical angle and C is the velocity of the directed wave (I) prior to the material surface (i.e. in the separating medium such as water or soft tissue, or both). Further, the method may include approximating the density of the solid (p') using the first identified critical angle ($\phi_1$) and the amplitude reflected at small angles. In still further enhancements, the method includes approximating Young's modulus of elasticity (E) or Poisson's modulus ($\sigma$) using the first and second critical angles corresponding to the first and second identified maxima. Further, the method may include identifying a third critical angle ($\phi_3$) occurring as a minima after the first critical angle ($\phi_1$) and is apparent as the amplitude of the reflected ultrasound waves (R) approaches 0. In other enhancements, particularly where the material under examination is not isotropic, the method includes an investigation of the full matrix of elasticity.

BRIEF DESCRIPTION OF THE DRAWINGS

FIG. 5 is a flow chart of the application software for the computer of FIGS. 3 and 4, where FIG. 5A describes the "Distance to Bone" subroutine, FIG. 5B describes the "Find Flat Spot" subroutine, FIG. 5C shows the "Locate Surfaces" subroutine, FIG. 5D illustrates the "Scan Bone" subroutine, FIG. 5E describes the "Signal Analysis" subroutine, and FIG. 5F illustrates the "Cross Comparison" subroutine.

DESCRIPTION OF THE PREFERRED EMBODIMENTS

Figure 1:
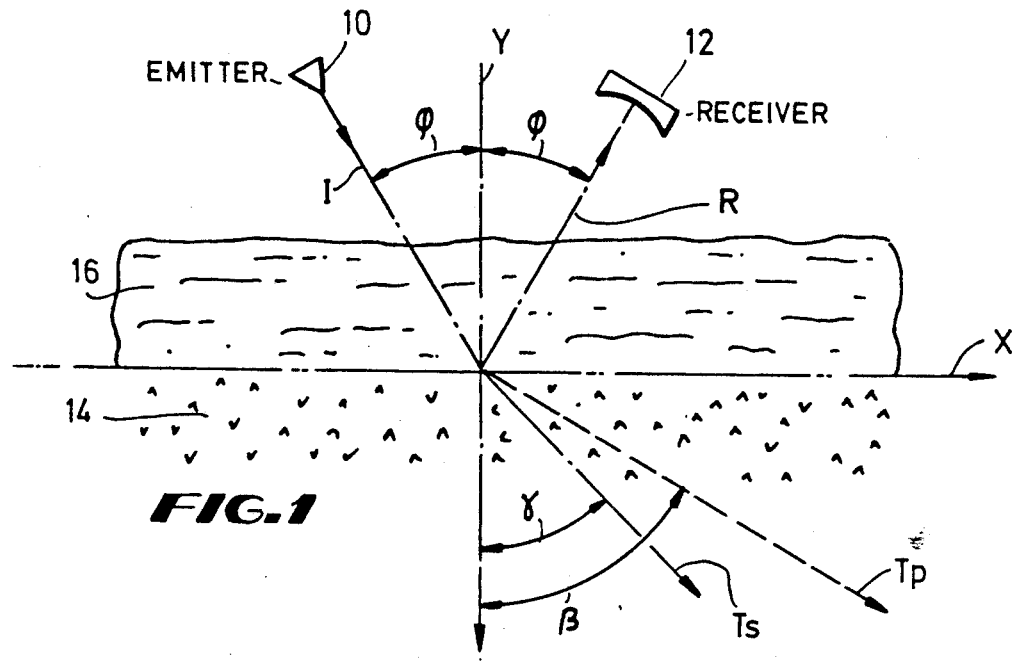
FIG. 1 is a schematic view of the propagation patterns of the ultrasound waves in the method of the present invention.
Figure 2:
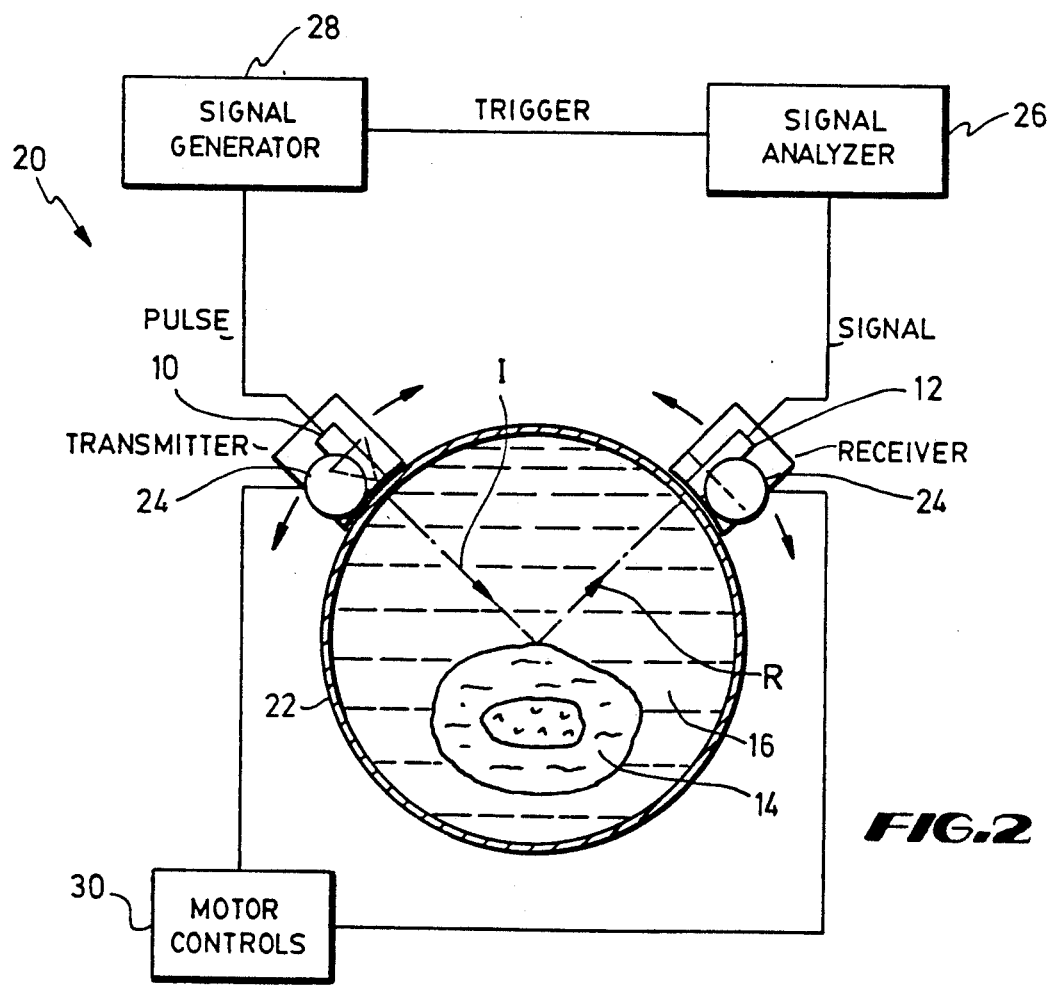
FIG. 2 is a schematic view of an apparatus in accordance with the present invention.

The method and apparatus of the present invention is useful in determining the physical properties of a variety of materials. Because the present invention principally investigates the amplitude of reflected ultrasound waves, the only material requirements are that the material under investigation reflect a significant ultrasound component and that the velocity of sound in it be greater than that of the first medium (e.g. water or soft tissue). FIGS. 1 and 2 illustrate the general critical angle of reflection method of the present invention and is useful in understanding the specific embodiments of FIGS. 3–5.

1. General Description

Many materials of interest have complex physical structures which makes analysis of the material's mechanical properties difficult, for example, because of nonhomogeneity or anisotropic structure. FIGS. 1 and 2 illustrate a simplification which is useful in explaining the approach and theory (without being bound by theory) of the present invention. That is, for purposes of generalized discussion, FIG. 1 neglects ultrasound attenuation phenomena, assumes that the material under investigation is isotropic, and assumes that the ultrasound waves are considered plane with the usual mathematical consequences of infinite extent and energy content. In a homogeneous, isotropic material two plane waves result: a longitudinal or pressure wave in which both the displacement and the velocity of displacement of particles in the material are parallel to the direction of propagation of the incident wave; and a transverse or shear wave, in which the displacement and velocity of displacement are perpendicular to the incident wave. In the present application "pressure wave" is used to denote both pure pressure waves and quasi-pressure waves in which the displacement and the velocity of the displacement are best characterized as being approximately parallel to the direction of propagation of the incident wave. "Shear wave" is used to denote pure shear wave or quasi-shear wave in which the displacement and its velocity are best characterized as being approximately perpendicular to the direction of propagation of the incident wave. Typically, shear wave velocity is 50% to 70% of the pressure waves velocity, particularly in homogeneous, isotropic materials.

FIG. 1 illustrates an ultrasound transducer 10 functioning as a transmitter and an ultrasound transducer 12 functioning as a receiver in which an ultrasound wave impinges upon a plane separating the material under investigation 14 (such as bone) from a separating medium 16 (such as soft tissue). For convenience the plane defined by the direction of propagation of the transmitted wave and the normal to the surface of the material 14 is defined as the XY plane in FIG. 1. The incoming or transmitted wave (I) upon arrival at the interface of the material 14 and medium 16 (YZ plane with X=0) gives rise to a reflected wave (R) redirected through the medium 16 to the receiver 12. For illustrative purposes, particle motion in FIG. 1 is seen to be constrained to the XY plane, so that the transmitted wave (I) gives rise to a pressure wave $T_p$ and shear wave $T_s$. The angle of refraction of the pressure wave $T_p$ is denoted as B, while the angle of refraction of the shear wave $T_s$ is Y. In FIG. 1, the angle of incidence of the transmitted wave (I) is $\phi$ and in the preferred embodiment the angle of reflection of the reflected wave (R) is about equal to the angle of incidence $\phi$.

The amplitudes of the displacement velocities corresponding to the pressure wave $T_p$ and shear wave $T_s$ are determined by conservation laws, which takes into account the properties of material 14 and medium 16 as follows:

(1) continuity of normal components of the displacement (displacements along the normal are equal on each side of the interface);
(2) continuity of normal components of the stresses;
(3) continuity of the normal components of the intensity vector (absence of energy absorption at the interface); and
(4) constant phase relationship between waves along the entire wave front.

Obeying such conservation laws, from FIG. 1 the angles are related by the following condition:

$$\frac{\sin \phi}{c} = \frac{\sin B}{v_p} = \frac{\sin \gamma}{v_s}$$

where c is the velocity of the transmitted wave (I) in the medium 16, $v_p$ is the velocity of the pressure wave $T_p$, and $v_s$ is the velocity of the shear wave $T_s$ in the material 14. Setting p as the density of medium 16, p' as the density of medium 14 and $$Z_o = \frac{pc}{\cos \phi} \quad Z_p = \frac{p'v_p}{\cos B} \quad Z_s = \frac{p'v_s}{\cos \gamma}$$

Then if the displacement velocity waves have normalized amplitudes, $I = 1$
(incident wave)

-continued $$R = \left( \frac{Z_p \cos^2 2\gamma + Z_s \sin^2 2\gamma - Z_o}{Z_p \cos^2 2\gamma + Z_s \sin^2 2\gamma + Z_o} \right)$$
(reflected wave)

$$T_p = 2pc \frac{\frac{\cos 2\gamma}{\cos \beta}}{(Z_p \cos^2 2\gamma + Z_s \sin^2 2\gamma + Z_o)}$$
(transmitted pressure wave)

$$T_s = -2pc \frac{\frac{\sin^2 2\gamma}{\cos \gamma}}{(Z_p \cos^2 2\gamma + Z_s \sin^2 2\gamma + Z_o)}$$
(transmitted shear wave)

The solution above applies for angles of incidence $\phi$ such that B does not exceed 90°. The value of $\phi_1$ for which B is equal to 90° ($\pi/2$) is given by:

$$\sin \phi_1 = \frac{c}{v_p}$$

$\phi_1$ is the first critical angle useful in the method of the present invention. When the angle of incidence $\phi$ is equal to the first critical angle $\phi_1$, it can be seen that $T_p = T_s = 0$, all the wave energy is reflected (reflection is a maxima, R=1).

A second critical angle $\phi_2$ has been found where the angle of incidence exceeds the first critical angle of $\phi_1$. At such increasing angles of incidence (still less than 90°) the amplitude $T_p$ represents a surface wave traveling parallel to the surface of the medium 16. The second critical angle $\phi_2$ occurs at a vanishing shear wave $T_s$ and is generally defined by sin $$\phi_2 = \frac{c}{v_s}.$$

The amplitude of the reflected wave R at $\phi_2$ (in terms $Z_p$ and $Z_o$) is:

$$R_2 = \frac{Z_p^2 - Z_o^2}{Z_p^2 + Z_o^2}$$

$Z_p$ is found using the (analytic continuation) formula:

$$Z_p = \frac{p'V_p}{\sqrt{\left[1 + \left(\frac{v_p}{c} \sin \phi_2\right)^2\right]}}$$

Theoretical examination predicts that at the second critical angle the transmitted shear wave vanishes ($T_s = 0$) and the absolute value of the reflected wave (R) is at or near a maximum. $\phi_2$ occurs either at a maximum ($R_2$ positive) or at an inflexion point ($R_2$ negative). In this latter case, $\phi_2$ falls between a zero (minimum) and a maximum.

Turning to FIG. 2 the schematic of an apparatus 20 in accordance with the present invention is illustrated. Broadly speaking, the apparatus 20 includes a means for transmitting an ultrasound wave (transducer 10) and a means for receiving the reflected ultrasound wave (transducer 12). A holding mechanism 22 positions the material under examination, while the separating medium 16 is interposed between the material 14 and transmitter and receiver 10, 12. In FIG. 2, the material 14 under examination is a bone, while the separating medium 16 includes water and soft tissue.

A stepping motor 24 is coupled to transmitter 10 and receiver 12 respectively, and is coupled to the holding mechanism 22 by a toothed circular rail (not shown). The stepping motors are operable through motor controls 30 to move the transmitter 10 and receiver 12 through an arc about the material 14.

The signal analyzer 26 is preferably a microcomputer, which periodically triggers the signal generator 28. Upon receiving the trigger, the signal generator 28 generates a pulse which is amplified and passed to the transmitter 10. The transmitter 10 upon receiving the pulse transmits the ultrasound wave (I) through the medium 16 at the material 14. The receiver 12 receives the ultrasound wave (R) reflected by the material 14. Preferably the transmitter 10 and receiver 12 are tuned to the same frequency.

During examination, the transmitter 10 and receiver 12 are initially positioned close to the normal to the material 14 (adjacent the Y axis as shown in FIG. 1). The transmitter 10 and receiver 12 are simultaneously stepped about the holding mechanism 22 so that the angle of incidence of the transmitted wave (I) is equal to the angle of reflection of the reflected wave (R). As shown in FIG. 1, this angle is denoted $\phi$ and preferably increases in the range from 0-90°, but useful investigations may be conducted using a more restricted range, e.g. to include only the first critical angle. As can be appreciated from FIG. 2, after each ultrasound transmitted wave (I), the motor controls 30 simultaneously steps the transmitter 10 and receiver 12 to a new position. Depending upon the number of measurements desired (i.e. resolution), the transmitter 10 and receiver 12 are preferably stepped in increments of a fraction of a degree. Thus, the receiver 12 generates a signal at each increment which is recorded by the signal analyzer 26 and represents the amplitude of the reflected wave (R) for a corresponding angle $\phi$. The result of this examination is a plot of reflected amplitude (ordinate) versus the angle of incidence $\phi$ (abscissa).

2. Moving Transducer System of FIG. 3

Figure 3:
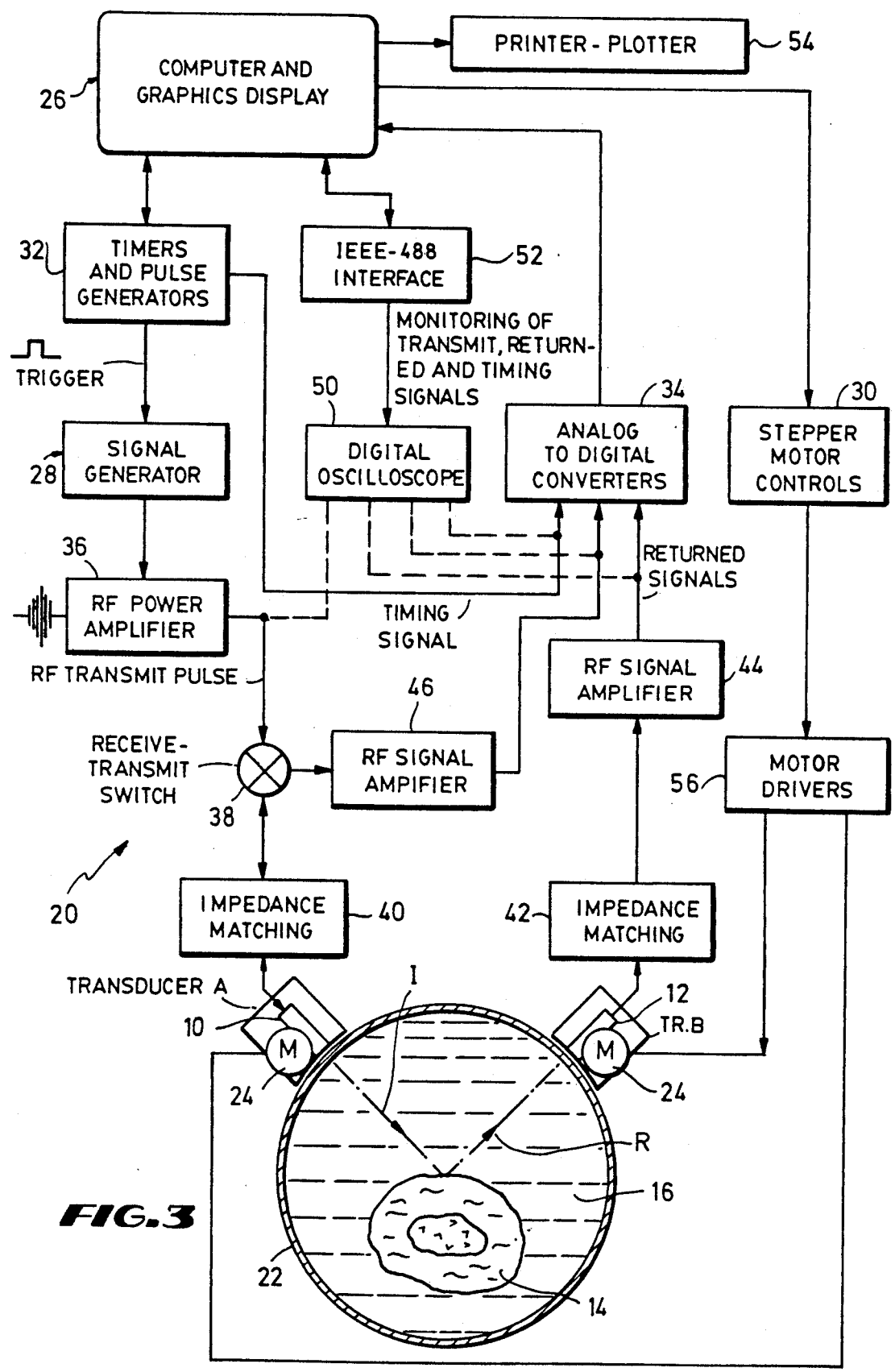
FIG. 3 is a schematic view showing in block diagram the components of a preferred embodiment of the apparatus of the present invention.

Turning now to FIG. 3, the preferred embodiment of the apparatus 20 of the present invention is illustrated in more detail. In the embodiment of FIG. 3, the transmitting transducer 10 is used as a signal transceiver, while the transducer 12 is used as a receiver only. The microcomputer 26 periodically generates a trigger signal through the timer and pulse generator 32. The timer 32 generates a trigger to the signal generator 28 as shown in the drawing, and additionally generates a signal which is simultaneously passed to the analog-to-digital converters 34. The signal generator 28 generates a signal which is amplified by RF power amplifier 36, with the amplified signal passing through transmit switch 38 to the impedance matching network 40.

As can be appreciated from FIG. 1, the ultrasonic wave pressure from the transmitted wave (I) is reflected from the material surface 14 as reflected wave (R) and received by the receiver 12. The receiver 12 transforms the reflected wave (R) into a return signal which is passed through an impedance matching network 42, amplified at power amp 44, and presented to the A to D converters 34 as a return (retarded) pulse. The A to D converters 34 generate a digital signal which is representative of the analog return signal from transducer 12.

As can be appreciated, if the transducer 10 is operated as a receiver, the switch 38 is toggled and the return signal amplified by the power amp 46 and presented to the A to D converters 34 in a similar fashion.

Digital oscilloscope 50 is used as needed and can be coupled as shown to the various circuits to verify, quantify and test signals in these circuits. Thus, the digital oscilloscope can monitor the amplified signal from the power amplifier 36, the return signals from the amplifiers 44, 46, as well as the timing pulse from the timer 32. The signals monitored by the digital oscilloscope 50 may be graphically presented through the IEEE-488 interface 52 on the graphic display of the computer 26. A printer/plotter 54 is provided as an output option from the computer 26.

The stepper motor controls 30 receive inputs from the computer 26 as shown to incrementally step the transducers 10, 12 about the material 14. As can be seen, the motor drivers 56 sense the input from the motor control 30 to synchronously, but independently, actuate the respective stepping motors 24 to move the transducers 10, 12. The transducers 10, 12 are preferably moved in incremental steps of fixed value and are at the approximately identical angle of incidence $\phi$ for each increment.

The holding mechanism 22 is adaptable for different uses, primarily dependent upon its size. For example, in the preferred embodiment of FIG. 3 a small, laboratory size system has been used for holding a single sample of polished bone or other material 14 in the water medium 16. This holding mechanism 22 has been found useful not only for experimental verification, but also for ex vivo analysis of samples and biopsies. Alternatively, a clinical system of the holding mechanism 22 has been devised in which the holding mechanism 22 is sufficiently large to receive portions of the human skeletal structure. This clinical system may be used for in vivo or in situ analysis and diagnosis of the tendency of bone to fracture, of bone healing, etc. Of course, different types of holding mechanisms 22 may be devised for holding different types of materials 14 other than bone.

3. Fixed Transducer Apparatus of FIG. 4

Figure 4:
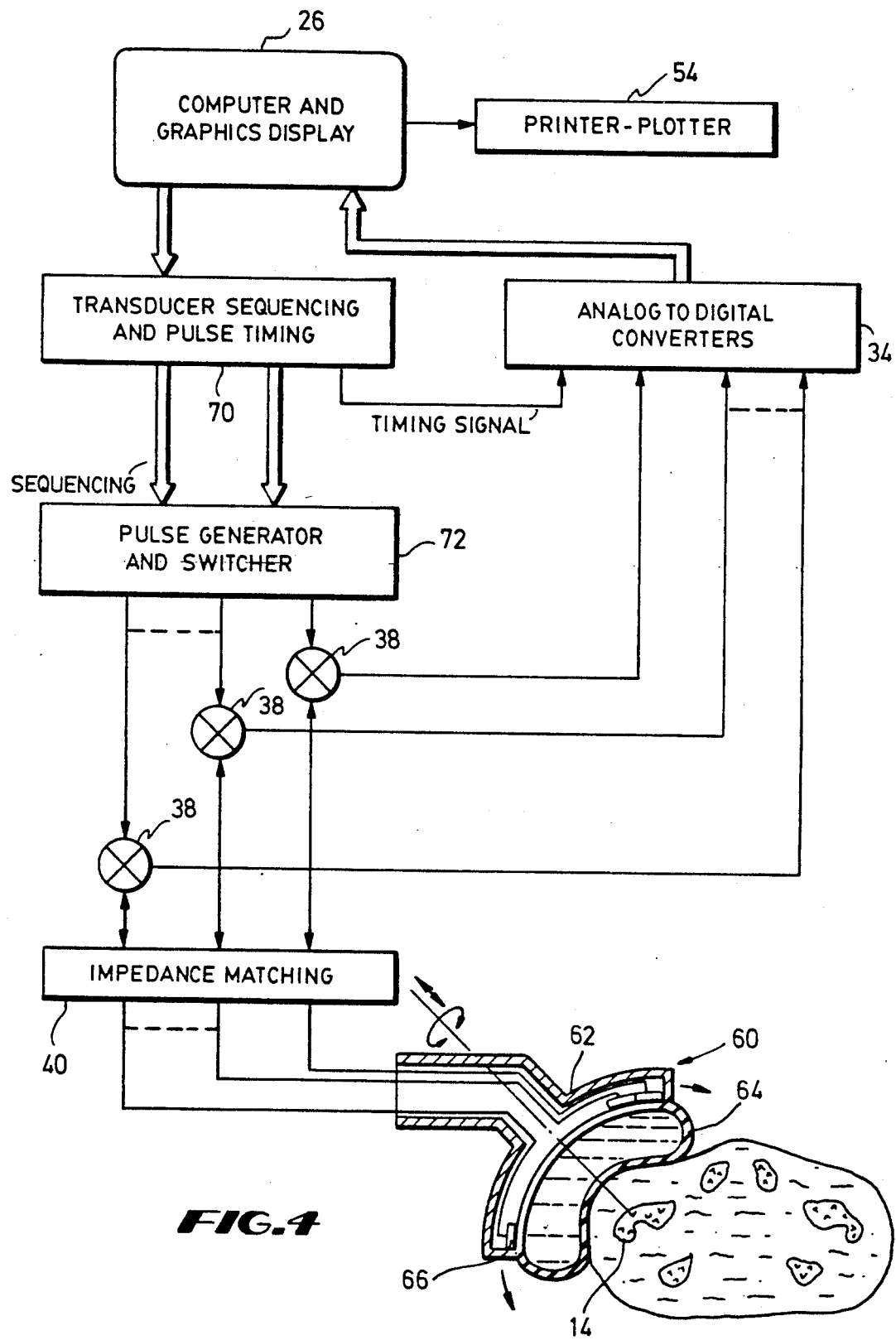
FIG. 4 is a schematic view showing in block diagram an alternative embodiment of the apparatus of the present invention.

Turning to FIG. 4, a block diagram of an alternative embodiment is illustrated in which the transducers are fixed and the control of transmission and reception made electronically rather than mechanically as illustrated in FIG. 3. In FIG. 4, in situ analysis of a material 14 (bone) is illustrated. A transceiver system 60 includes an applicator head 62 which is capable of three dimensional adjustment motion (as shown by the direction arrows in FIG. 4). Although the applicator head 62 of FIG. 4 is manually adjustable, computer adjustment control is a desirable alternative. As can be seen, a pressurized, temperature control water bag or water bolus 64 is interposed between the applicator head 62 and patient, assuring good contact and match with the surface of the body of the patient. The applicator head 62 is positioned so that its focal point on the bone surface and its axis is aligned with the axis of the normal to the bone surface 14 at the point of interest as illustrated in FIG. 4.

The transceiver system 60 incorporates a circular transducer array comprising eighty small ($\frac{1}{4}$ inch by $\frac{1}{4}$ inch) transducers 66. As can be appreciated, with the transceiver system 60 positioned in a desired location adjacent the patient, the transducers 66 can be electronically activated alternatively as transmitters or receivers as desired. Preferably, the transducers 66 are sequentially activated one at a time as a transmitter, or may be activated in a small group to give better definition of sound wave as it intersects with the bone 14. After a transducer 66 pulse, the transducers will be switched to act as receivers for the reflected sound energy of the reflected wave (R).

Sequence and timing mechanism 70 is provided which upon receiving trigger signal from the computer 26 selects which transducer 66 (or group) will be pulsed and the duration of the pulse. The timing signal at the beginning of the pulse is also supplied to the A/D converter section 34. The pulse generator and switcher 72 generates and amplifies the signal which is directed through a specific lead line and switch 38 and impedance matching network 40, to a specific transducer 66 (or small group of transducers). As soon as the transmitted wave (I) is generated from the activated transducer 66, the pulse generator and switcher 72 toggles the switches 38 to convert the transducers 66 to receive operation. Thus, all eighty transducers are acting as receivers for the reflected wave (R). The return signals indicative of the reflected wave (R) will pass through the A/D convertors 34, digitized, and presented to the computer 26 for processing and presentation.

4. Operation and Processing

FIG. 5 represents the flow charts for the operating software of the computer 26 of FIG. 3. FIG. 5 illustrates the main program or program overview, while FIGS. 5A–5F illustrate the subroutines as indicated. As can be seen from FIGS. 5 and 5A, the first subroutine is designed to determine the distance from the transducer 10 (or transducer "A") to the bone 14. This is easily accomplished using the apparatus 20 of FIG. 3, by operating the transducer 10 alternately in the transmit and receive mode. As can be seen from FIG. 5A, the patient or bone 14 is first manually positioned in the holding mechanism 22 and the transducer 10 manually positioned in a direct vertical orientation to the bone as viewed in FIG. 3. The transducer 10 is then pulsed and the echoes received with the lapsed time determinative of the distance to the bone 14. Distance to the bone can be calculated for each incremental increase in the angle of incidence $\phi$ (transducer 10 positioned in the arc about bone 14 as in FIG. 2 or by moving the applicator head 62 as in FIG. 4).

After the completion of subroutine 5A, the program proceeds to subroutine "FIND Flat Spot" as illustrated in FIG. 5B. The distance to the bone calculated at various increments from the subroutine "Distance To Bone" are graphically displayed as an image on the computer 26 and correlated to find a relatively smooth, flat spot for evaluation. Once such a relatively flat spot is located, patient movement is prohibited and the transducers are positioned for evaluation of the flat spot, i.e. at a distance such that this spot is at the center of rotation and taking the normal to the flat spot as the axis of symmetry of transducer motion in a given plane (direction). The direction of the plane can be varied.

The programs next step to subroutine "Locate Surfaces" illustrated in FIG. 5C, which is designed to locate the surfaces separating various media (tissues) which intervene between the transducers and bone surface. The transducer 10 is first positioned at a relatively small angle of incidence $\phi$ and the transmitted signal (I) initiated (pulsed). The reflected signal (R) is received, digitized, and stored on computer 26 before stepping the transducer 10 in the arc about the bone 14. Note from FIG. 5C that after the arc is completed and the digitized amplitude of the echo return signals stored, the various patient tissues are identified. That is, the patient surface, bone surface, and other intervening tissue boundaries (muscle, fat) are located, attenuation and scatter coefficients are assigned for each respective tissue, and the angle dependent attenuation thicknesses and beam path calculated. Thus, the "Locate Surfaces" subroutine primarily identifies the intervening tissue boundaries so that tissue attenuation and the ray path followed by the incident and reflected waves can be identified.

The next subroutine is illustrated in FIG. 5D and performs the "Scan Bone" routine to generate the primary raw data. As can be seen in FIG. 5D, the transmitted wave (I) is generated and the reflected wave (R) is received for each increment in angle of incidence $\phi$. The distance from transducer 10 to the patient surface and bone surface is retrieved and the time of flight calculated for both the transmitted wave (I) and reflected wave (R). These are compared to the information obtained in the previous routine to check for patient movements. If no movement occurred, the "Scan Bone" subroutine then calculates bone echo amplitude corrected for attenuation in the intervening tissues and stores the digitized echo amplitude. The "Scan Bone" subroutine loops until the scan is complete. If more scans at the same site but along different directions are desired, the program loops back to "Locate Surfaces" until all desired scan directions are completed. Once all selected scan sites and scan directions are completed, the signal analysis (FIG. 5E) is initiated.

Turning to FIG. 5E, the "Signal Analysis" subroutine is depicted. The stored amplitude data as a function of angle of incidence $\phi$ is retrieved for a particular scan, and peak and edge detector algorithms applied. The first peak or "maxima" detected identifies the first critical angle. Preferably, the second critical angle is also identified as a second maxima following the first maxima. The "Signal Analysis" subroutine then calculates the bone matrix orientation, various bone velocities along major axes (shear velocities and pressure velocities), and the matrix of coefficients of elasticity (Young's and Poisson's modulus for isotropic materials), and density. If more sites are to be evaluated, then the program is repeated by returning to the "Distance To Bone" subroutine (FIG. 5A). However, if the sites have all been evaluated, the "Cross Comparison" subroutine of FIG. 5F is entered.

As can be seen from FIG. 5F, the user has several options for generating hard copy record on the printer/plotter 54. First, the user may plot the mechanical properties summary for each site—that is the bone matrix orientation, velocity, matrix of elasticity, and density. Next, the user may cross compare mechanical properties for the different sites for which data has been taken to look for strength variations. Microfracture evidence may be readily compared at different sites. Finally, the summary can be printed or plotted.

5. Examples

Experiments have been undertaken to confirm the presence of critical angles of incidence corresponding to reflected amplitude maxima which are useful in approximating mechanical properties of material. First, simple isotropic, poorly absorptive materials (acrylic and aluminum) are examined. Next, bone has been examined, first assuming the bone is isotropic and next under various assumptions of anisotropy. Generally, the system configuration was similar to FIGS. 2 and 3.

Example-Acrylic

A sample of acrylic 14 was placed within the holding mechanism 22 with water constituting the medium 16. The water has velocity (about 1480 meters per second at 21° C.) and density which are known (and close to that of soft tissue, which makes analysis of bone easier).

The transducers 10, 12 were simultaneously stepped through increasing angles of incidence about the acrylic sample 14. In this experiment, the angle of incidence $\phi$ was only stepped through the range 9°–40° therefore producing the results illustrated in FIG. 6.

Figure 6:
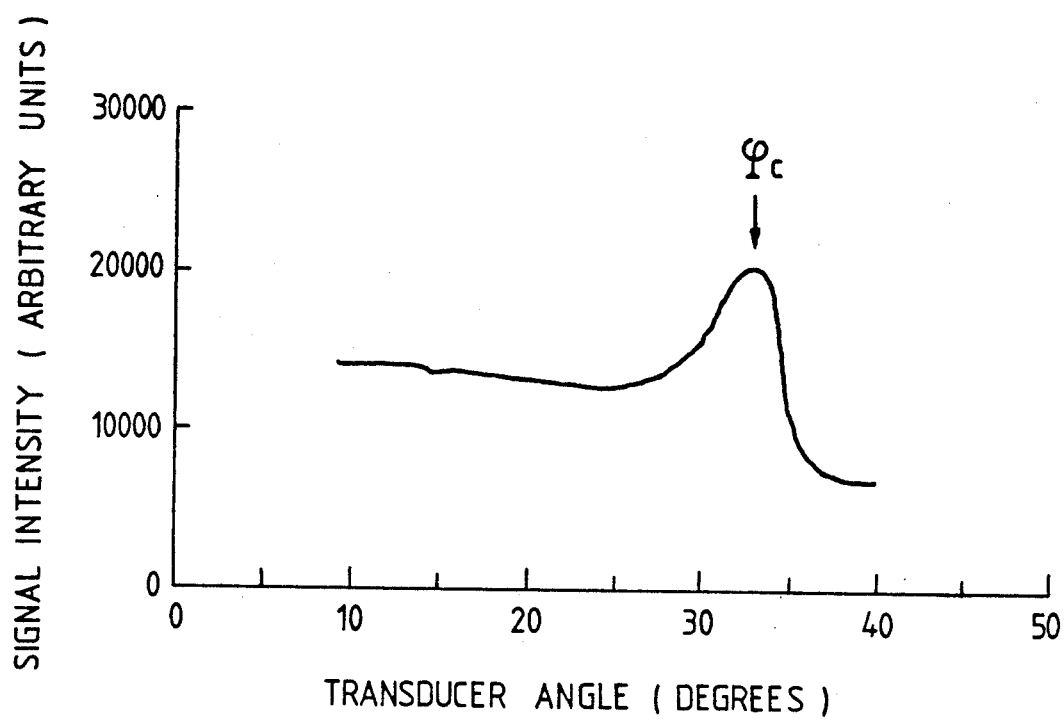
FIG. 6 is a graph illustrating signal intensity as a function of transducer angle in a sample of acrylic.

As can be seen in FIG. 6, the reflected amplitude has a first maxima at about 33° plus or minus 0.5°. The present invention predicts that the pressure wave velocity ($v_p$) can be approximated as follows:

$$v_p = \frac{c}{\sin \phi_1}$$

Using this relationship, the pressure wave velocity for acrylic is calculated as approximately 2,717 plus or minus 40 meters per second. This approximation is found to be close to the normally accepted value of 2,680 meters per second.

Example-Aluminum

Figure 7:
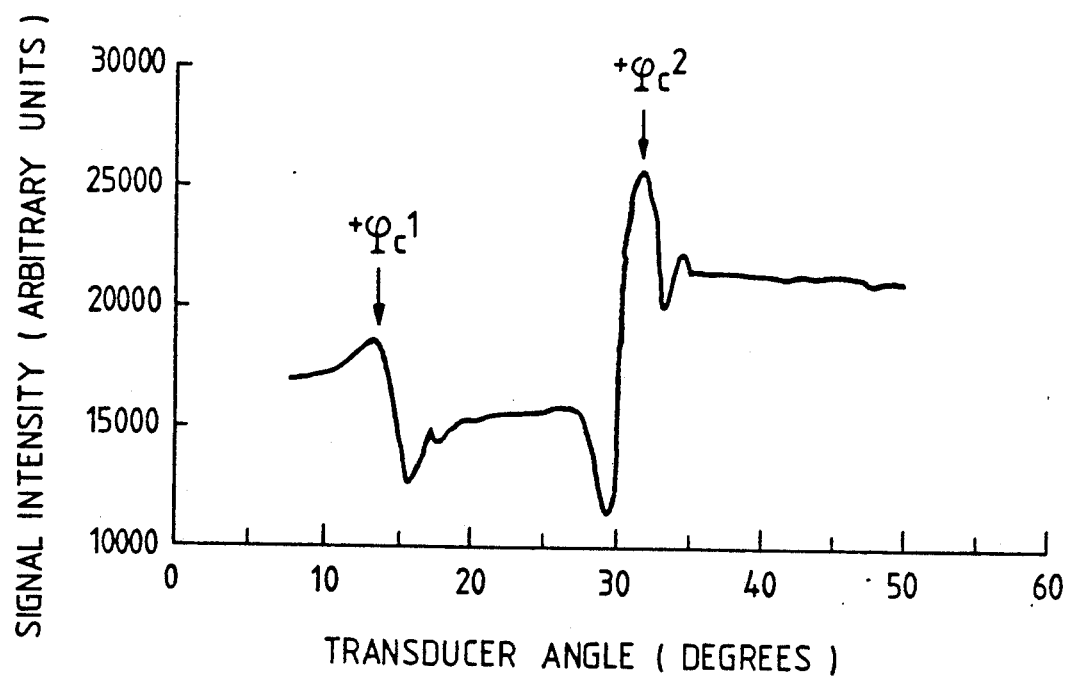
FIG. 7 is a graph illustrating signal intensity as a function of transducer angle in a sample of aluminum.

The above process was repeated with aluminum substituted as the material 14 in a water bath medium 16. FIG. 7 illustrates reflecting wave signal intensity resulting from an angle of incidence being increased from about 8°–50°.

The first prominent maxima, shown in FIG. 7, occurs at about 13.5° and is indicative of the first critical angle of $\phi_1$ while the second maxima occurs about 31.8° and is indicative of the second critical angle by $\phi_2$. Using the relationship:

$$v_p = \frac{c}{\sin \phi_1}$$

gives $v_p = 6,340$ meters per second plus or minus 120 meters per second. Using the relationship:

$$v_s = \frac{c}{\sin \phi_2}$$

yields 2,809 meters per second plus or minus 29 meters per second. From the literature, $v_p$ normally falls in the range of 6,300–6,420 meters per second and $v_s$ is about 2,980 meters per second, in close agreement with the experimental data obtained.

For isotropic materials, the present invention predicts density, Young's modulus (E) and Poisson's modulus ($\sigma$) as follows:

$$\rho' = \frac{1}{v_p} \rho c \frac{1 + \frac{R}{I_o}}{1 - \frac{R}{I_o}}$$

$$\frac{E}{\rho} = v_s^2 \frac{3v_p^2 - 4v_s^2}{v_p^2 - v_s^2}$$

-continued $$\sigma = \frac{v_p^2 - 2v_s^2}{2(v_p^2 - v_s^2)}$$

from the experimental data the calculations yield:
$E/\rho = 26.50 \times 10^6$ (meters per second)$^2$ or
$E = 7.16 \times 10^{10}$ newtons per meter$^2$ ($\rho = 2.7$ g/cm$^3$)
$\sigma = 0.38$ The above experimentally derived values for Young and Poisson's modulus are close to the normally accepted values of $7.1 \times 10$ N/m$^2$ (E) and 0.355($\sigma$).

It should be noted that the experiment was also repeated for brass, and a first critical angle obtained at $\phi_1 = 18.3°$ giving a pressure wave velocity ($v_p$) of 4,714 meters per second, which compares well with the accepted value of $v_p = 4,700$ meters per second.

Example-Bone (Isotropic Assumption)

The sample of polished, preserved bone (4.5 cm × 1.8 cm × 0.42 cm) was examined using the method of the present invention. Because of equipment limitations, only angles than 50° were investigated, allowing only the first critical angle $\phi_1$ to be obtained. The bone was first examined along its shorter axis illustrates the results obtained when the apparatus of FIG. 3 was used.

Figure 8:
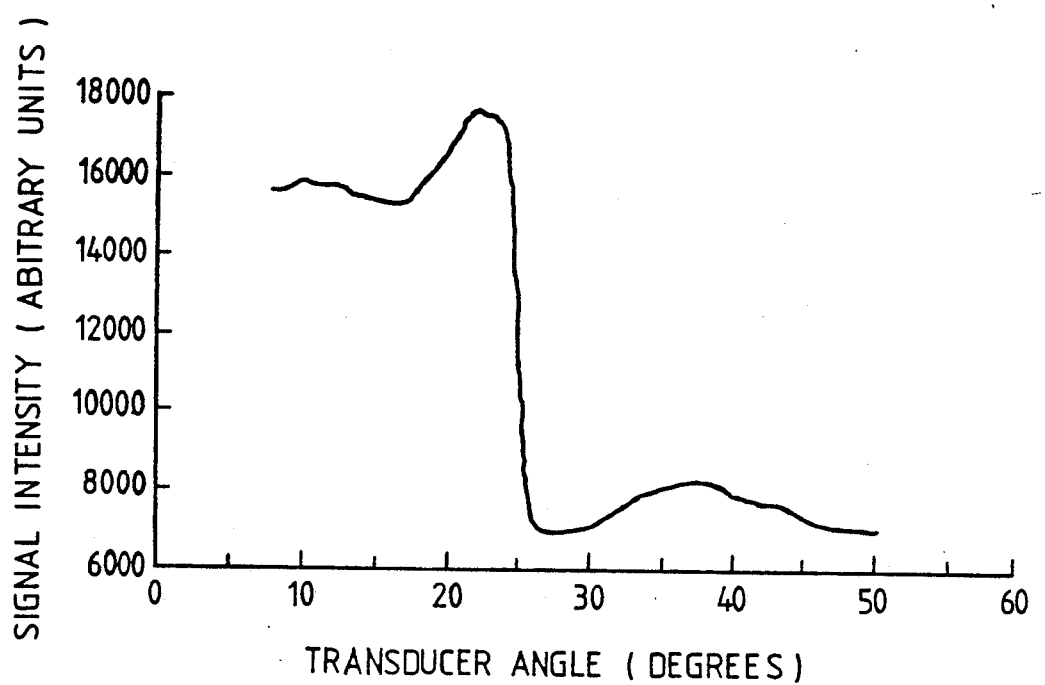
FIG. 8 is a graph illustrating signal intensity as a function of transducer angle along the shorter axis of polished, preserved bone.

As can be seen in FIG. 8, the prominent maxima occurs at about 22.2° with an edge (value at ½ maxima) at 25°.

As can be seen in FIG. 8, the maxima is less pronounced and the edge is now at about 29°. The critical angles measure only velocities corresponding to the principal axes parallel to the surface. Relative amplitudes, on the other hand, have values dependent upon the velocities along the radial direction as well. Therefore, two different pressure wave velocities must be considered because of this bone anisotropy. It is clear that the smaller velocity occurs in the first, but not the second experiment. Computing, $v_p^1 = 3,917$ meters per second and $v_p^2 = 3.352$ meters per second. The second value, $v_p^2$, is estimated using the difference between the edges (4°) in the two orientations as a measure of the difference between the two critical angles. Values found in research on dry human bone are: $v_p^0 = 3,970$ meters per second (axial) and $v_p^1 = 3,300$ meters per second (radial), in close agreement with the experimental data obtained. See, S. Lees, *Sonic Properties of Mineralized Tissues*, in TISSUE CHARACTERIZATION WITH ULTRASOUND, Vol. II, pp. 2077–226 (J. Greenleaf ed. 1986).

Example-Bone (Transverse Symmetry Assumption)

Deviations from the isotropic scattering amplitudes are particularly strong in cortical bone and are of importance in analyzing the potential to resist fracture. As the condition of symmetry is relaxed from an assumption of isotropy to that of transverse symmetry (isotropy violated in only one direction) the number of elastic parameters increases from two to five.

Turning to FIG. 2, with x denoting the radial direction, y the tangential direction, and z the longitudinal direction, the five independent elements of the matrix of elasticity are $C_{11}$, $C_{12}$, $C_{13}$, $C_{33}$, and $C_{44}$. Typical values for these constants of elasticity for cortical bone (femur) can be found in R. Ashman, S. Corvin, W. VanBuskirk, and J. Rice, *A Continuous Wave Technique for the Measurement of the Elastic Properties of Cortical Bone*, Journal of Biomechanics 17:349-361 (1986). Considering scattering only the XY plane, only two terms of the matrix are involved—$C_{11}$ and $C_{12}$. The case of waves in XY plane is formally identical to the isotropic case. The velocity of the pressure wave is $$v_p \text{ is } \sqrt{\frac{C_{11}}{p}}$$

and the velocity of the shear wave $$v_s \text{ is } \sqrt{\frac{C_{11} - C_{12}}{2p}}.$$

The structure of the conservation laws in each of the three regions separated by $\phi_1$ and $\phi_2$ is instructive. In the first region (angles of incidence $< \phi_1$), phase conservation demands that:

$$\frac{\sin \phi}{c} = \frac{\sin B}{v_p} = \frac{\sin \gamma}{v_s}$$

In the second region, an analytic combination of these formulae can be obtained by substituting the hyperbolic cosine of a variable b, Chb, for sin B. Similarly, in the third region, Chg can be substituted for sin $\gamma$. The regions are separated by two critical angles $\phi_1$ and $\phi_2$. The first critical angle is given by $$\sin \phi_1 = \frac{c}{v_p}, \text{ the second by } \sin \phi_2 = \frac{c}{v_s}$$

as previously discussed.

The conserved quantities—the normal components of the displacement velocities and of the stress tensor—result in the following sets of equations in each of the three regions In the first, $$0 \leq \phi \leq \phi_1$$
$$1 - R = \frac{\cos \beta}{\cos \phi \cos 2\gamma} T_p$$

$$1 + R = \left( \frac{\rho' v_p}{\rho c} \cos 2\gamma + 4 \frac{\rho' v_s}{\rho c} \frac{\cos \beta \cos \gamma \sin^2 \gamma}{\cos 2\gamma} \right) T_p$$

$$T_s = -2 \frac{\sin \gamma \cos \beta}{\cos 2\gamma} T_p$$

In particular, when $\phi = 0$ $$1 - R = T_p$$

$$1 + R = \frac{\rho' v_p}{\rho c} T_p$$

$$T_s = 0 \quad \text{or}$$

$$R = \frac{\rho' v_p - \rho c}{\rho' v_p + \rho c}$$

When $\phi = \phi_1$ on the other hand, $$R = +1$$

$$T_s = 0$$

-continued
$$T_p = \frac{2\rho c}{\rho' v_p \cos 2\gamma}$$

In the first region $2\gamma$ remains positive in bone. The case $\cos 2\gamma = 0$ would appear to introduce a singularity, but further inspection of the explicity solution (isotropic solution) shows that its only effect is a change in sign of $T_p$, whereas $T_s$ and R are not affected by this zero.

In region 2 ($\phi_1 < \phi < \phi_2$)

$$1 - R = -i \frac{Sh\ b}{\cos \phi \cos 2\gamma} T_p$$

$$1 + R = \left( \frac{\rho' v_p}{\rho c} \cos 2\gamma - 4i \frac{\rho' v_s}{\rho c} \frac{Sh\ b \cos \gamma \sin^2 \gamma}{\cos 2\gamma} \right) T_p$$

$$T_s = 2i \frac{\sin \gamma\ Sh\ b}{\cos 2\gamma} T_p$$

It should be noted that these amplitudes are complex, but that the invention detects only parts of the amplitudes. It may be seen that at the first critical point Sh b=0, Ch b=1, the system reduces to $$\begin{cases} 1 - R = 0 \\ 1 + R = \frac{\rho' v_p}{\rho c} \cos 2\gamma\ T_p \\ T_s = 0 \end{cases}$$

This system is satisfied by the solution to the previous system (equations when $\phi = \phi_1$) showing continuity across the first critical point. At the second critical point $$\begin{cases} 1 - R = +i \frac{Shb}{\cos \phi} T_p \\ 1 + R = -\frac{\rho' v_p}{\rho c} T_p \\ T_s = -2i\ Sh\ b\ T_p \end{cases}$$

The real parts of the first two equations are $$1 - Re\ R = -\frac{Shb}{\cos \phi} Im\ T_p$$

$$1 + Re\ R = -\frac{\rho' v_p}{\rho c} Re\ T_p$$

while the imaginary parts are $$Im\ R = \frac{Shb}{\cos \phi} Re\ T_p$$

$$Im\ R = -\frac{\rho' v_p}{\rho c} Im\ T_p$$

with solution $$\begin{cases} Re\ T_p = -\dfrac{2}{\dfrac{\rho' v_p}{\rho c} + \dfrac{\rho c}{\rho' v_p}\left(\dfrac{Sh\ b}{\cos \phi}\right)^2} \\ Re\ R = 1 - \dfrac{2\dfrac{Sh\ b}{\cos \phi}}{\dfrac{\rho' v_p}{\rho c} + \dfrac{\rho c}{\rho' v_p}\left(\dfrac{Sh\ b}{\cos \phi}\right)^2} \end{cases}$$

It will be seen that the reflected signal, ReR, may be positive or negative. If ReR changes sign in this region, as the receiver is not sensitive to a change of sign (to the phase of R) then the zero (the point at which ReR changes sign) will appear as a minimum of the reflected amplitude, at an angle preceding the second critical angle. This zero is considered a third critical angle $\phi_3$ occurring at a "minima" reflecting amplitude between the first and second critical angles $\phi_1$, $\phi_2$.

In region 3 ($\phi > \phi_2$) the conservation laws become $$1 - R = -i\dfrac{Shb}{\cos \phi\ (2Ch^2g - 1)} T_p$$

$$1 + R = \left[-\dfrac{\rho' v_p}{\rho c}(2\ Ch^2g - 1) + \dfrac{4\rho' v_s}{\rho c}\dfrac{Sh\ b\ Ch^2g\ Sh\ g}{2\ Ch^2g - 1}\right] T_p$$

$$T_s = -i\dfrac{v_s}{v_p}\dfrac{2\ Sh\ b\ Ch\ b}{2\ Ch^2g - 1} T_p$$

The value of the reflected amplitude at the second critical point ($\phi_2$) is the solution to the system (g=0)

$$\begin{cases} 1 - R = -i\dfrac{Sh\ b}{\cos \phi} T_p \\ 1 + R = \left[-\dfrac{\rho' v_p}{\rho c}\right] T_p \\ T_s = 0 \end{cases}$$

which divides into:

a real part $$\begin{cases} 1 - ReR = \dfrac{Sh\ b}{\cos \phi} ImT_p \\ 1 + ReR = -\dfrac{\rho' v}{\rho c} Re\ T_p \end{cases}$$

and an imaginary part $$\begin{cases} ImR = +\dfrac{Sh\ b}{\cos \phi} ReT_p \\ ImR = -\dfrac{\rho' v_p}{\rho c} ImT_p \end{cases}$$

The reflected amplitude assumes the form $$ReR = 1 - \dfrac{2}{1 + \left(\dfrac{Z_p}{Z_o}\right)^2} = \dfrac{Z_p^2 - Z_o^2}{Z_p^2 + Z_o^2}$$

The solution is again continuous across this critical angle. Finally, when $\phi$ reaches its extreme value (90°) the real part of R approaches the value $-1$. (For $\cos\phi=0$, $ImT_p=ImR=0$, ReR$=-1$.) Because the reflected amplitude changes sign between the first critical angle and 90°, it definitely must have a zero, either in region 2 or in region 3. The angle $\phi_o$ at which the reflected amplitude is zero can be found by numerically solving one of the two following equations between impedances:

$$\rho' = \dfrac{\rho c}{\cos \phi_o} * \left[\left(\dfrac{v_s}{\cos \gamma_o}\sin^2 2\gamma_o\right)^2 + \left(\dfrac{v_p}{Shb_o}\cos^2 2\gamma_o\right)^2\right]^{-\frac{1}{2}}$$

(if the zero occurs in the second region)

$$\rho' = \dfrac{\dfrac{\rho c}{\cos \phi_o}}{\left|\dfrac{v_p}{Shb_o}Ch^2g_o - \dfrac{v_s}{Shg_o}Sh^2 2g_o\right|}$$

(if the zero occurs in the third region)

As $v_p$ and $v_s$ are known, these equations determine the bone density under the additional conditions:

$$\dfrac{v_p}{Chb_o} = \dfrac{c}{\sin \phi_o}$$

and:

$$\dfrac{v_p}{\sin \gamma_o} = \dfrac{c}{\sin \phi_o} \text{ or } \dfrac{v_s}{Ch\ g_o} = \dfrac{c}{\sin \phi_o}$$

Figure 10:
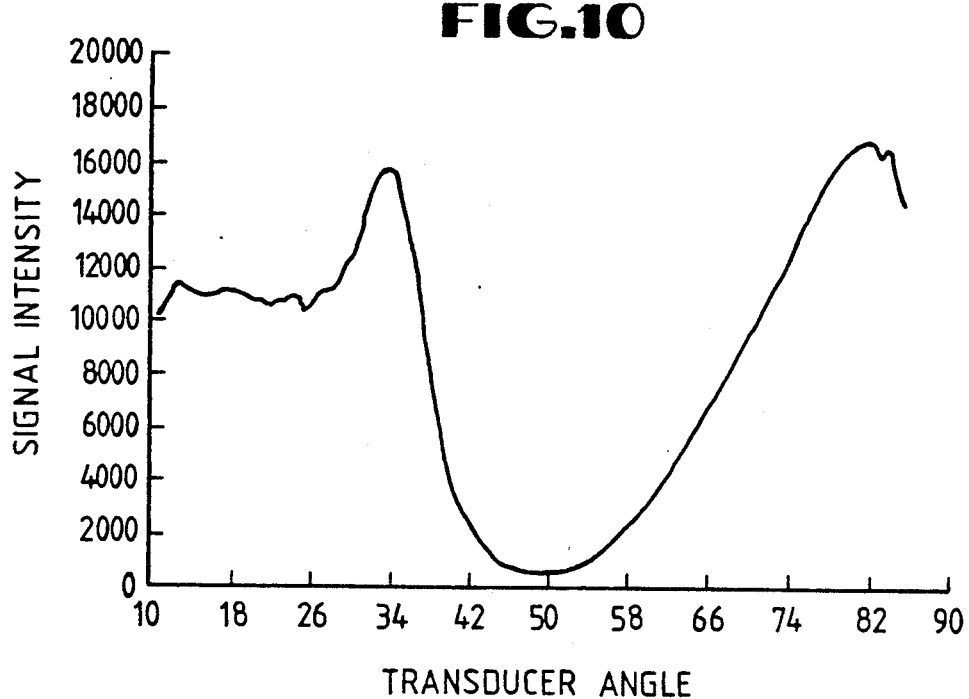
FIG. 10 is a graph showing signal intensity as a function of transducer angle along the shorter axis of a machined human femur.

FIG. 10 shows the experimental results of a scan of a machined human femur in a transverse cross sectional plane. The reflected amplitude shows a simple profile with a first critical angle (maxima) at 33°, followed by a decline and subsequent rise to a second critical angle at 82° with an inflection point at 77°. This is in turn followed by a rapid drop as the angle of reflection approaches unity. The results are interpreted as giving:

$$v_p{}^{xy}=2.717\pm80\ m/sec\ v_s{}^{xy}=1,495\pm11\ m/sec$$

Figure 11:
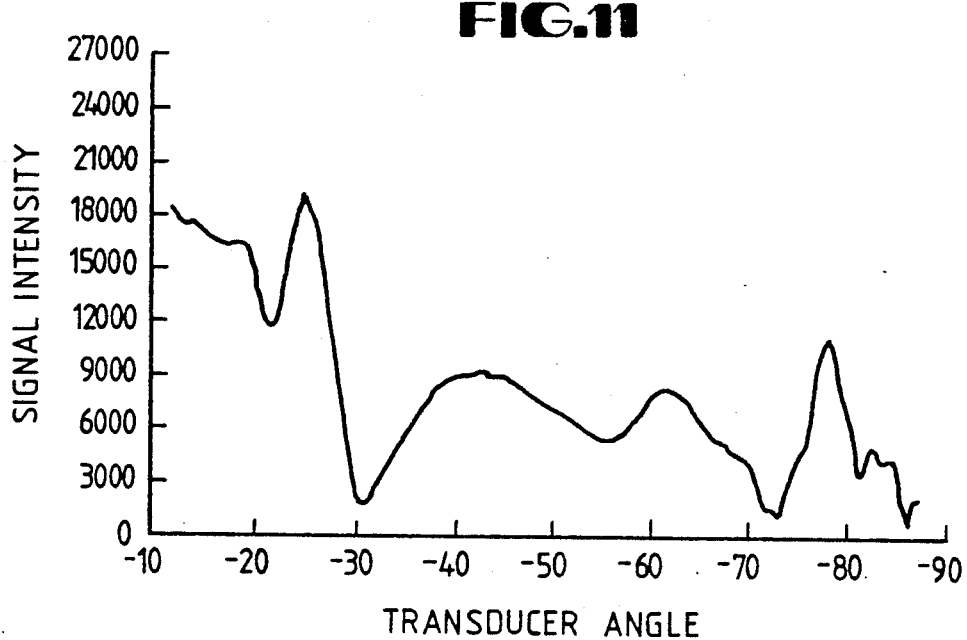
FIG. 11 is a graph showing signal intensity as a function of transducer angle along the longer axis of a machined human femur.

A longitudinal scan shows greater complexity but can be interpreted in a similar fashion. The experimental results of the longitudinal scan are shown in FIG. 11: The maxima in reflected amplitude at 24.7° and the maxima at 61.24° correspond to the first and second critical angles ($\phi_1$, $\phi_2$). The minima at 72° corresponds to the third critical angle ($\phi_3$). The final peak is an artifact due to the geometric penumbra in this configuration. Our method provides the following:

$$p=2.0\pm0.1\ g/cm^3$$

$$v_p{}^{xz}=3.589\pm66\ m/sec$$

$$v_s{}^{xz}=1.711\pm26\ m/sec$$

From these we derive $C_{11} = 16.03 \pm 0.66$ Gpa $C_{13} = 7.03 \pm 0.42$ Gpa $C_{33} = 25.77 \pm 1.03$ Gpa $C_{44} = 5.86 \pm 0.23$ Gpa The above results are about 10% smaller than those derived in R. Ashman, S. Corvin, W. VanBuskirk, and J. Rice, *A Continuous Wave Technique for the Measurement of the Elastic Properties of Cortical Bone*, Journal of Biomechanics 17:349–361 (1986) for fresh bone. The difference can be accounted for in view of the fact that this sample was machined and preserved, and thus had reduced density and strength, while Ashman's results were obtained for fresh bone.

Example-Bone (Hexagonal Symmetry)

The most accurate measurement of the elastic constants compares reflected amplitude as a function of the angle of incidence (and reflection) $\phi$, as well as of the angle between the plane of scattering and the plane containing the normal and the intrinsic z-axis of bone (direction of the scan) Both angles vary between 0 and $\pi/2$. This procedure results in the most extensive application of the present invention to the measurement of bone properties. The measurements of the two critical angles in a number of planes at different directions is capable of giving all elasticity constants under the assumption of hexagonal or transverse symmetry. Indicating with p' the local density of bone and $v_c$ the (constant) velocity in soft tissue, under the assumption of hexagonal symmetry:

$$\rho' \frac{v_c}{\sin^2 \phi_1} = \cos^4 \xi\, C_{33} + 2\sin^2 \xi \cos^2 \xi\, (C_{13} + 2C_{44}) + \sin^4 \xi\, C_{11}$$

$$\rho' \frac{v_c^2}{\sin^2 \phi_2} = \cos^2 \xi\, C_{44} + \frac{1}{2} \sin^2 \xi\, (C_{11} - C_{12})$$

which can be patently solved in terms of the five elasticity constant if p' is known. For instance, if just three angles are used $$\rho' = \frac{\rho_0 v_c}{\cos \phi_0}$$

$$\left(\xi = 0, \frac{\pi}{4} \text{ and } \frac{\pi}{2}\right)$$

the following system gives a solution in terms of the constants divided by p':

$$V_p^1 = \frac{v_c}{\sin \phi_1},\ v_s^1 = \frac{v_c}{\sin \phi_2} \text{ for } \xi = 0 \quad \text{Eqn H.1}$$

$$V_p^2 = \frac{v_c}{\sin \phi_1},\ v_s^2 = \frac{v_c}{\sin \phi_2} \text{ for } \xi = \frac{\pi}{4} \quad \text{Eqn H.2}$$

$$V_p^3 = \frac{v_c}{\sin \phi_1},\ v_s^3 = \frac{v_c}{\sin \phi_2} \text{ for } \xi = \frac{\pi}{2} \quad \text{Eqn H.3}$$

$$\frac{c_{11}}{\rho'} = (V_p^3)^2 \quad \text{Eqn H.4}$$

$$\frac{c_{33}}{\rho'} = (V_p^1)^2 \quad \text{Eqn H.5}$$

$$\frac{C_{44}}{\rho'} = (V_s^1)^2 = (V_s^2)^2 - \frac{1}{8}\left(\frac{C_{11} - C_{12}}{\rho'}\right) \quad \text{Eqn H.6}$$

$$\frac{C_{12}}{\rho'} = \frac{C_{11}}{\rho'} - 2(V_s^3)^2 \quad \text{Eqn H.7}$$

$$\frac{C_{13}}{\rho'} = 2(V_p^2)^2 - \frac{C_{33}}{2\rho'} - 2\frac{C_{44}}{\rho'} - \frac{C_{11}}{2\rho'} \quad \text{Eqn H.8}$$

In fact, Eqn H.6 shows that the system is over-constrained. Measurement at a larger number of angles $\xi$ allows optimization using constraints to minimize errors. Density remains an explicit unknown, which needs for its solution the measurement of a quantity which depends upon a term $pV^2$, where V can be independently measured from the first and second critical angles.

Such a measurement is given by the third critical angle $\phi_3$ in the reflected amplitude. If, for example, at an angle $\xi$, the third critical angle $\phi_3$ is found at an angle $\phi_o$ in region 3, the density can be found by solving the equation $$\frac{\cos \phi_0}{\rho_0 v_c}\, |2\, Shg\, Chg\, Shb\, Chg(C_{13}\cos^2 \xi + C_{12}\sin^2 \xi - C_{11}) +$$

$$(Ch^2g + Sh^2g)[-C_{11}Sh^2b + Ch^2g(C_{13}\cos^2 \xi + C_{12}\sin^2 \xi)]| =$$

$$|2v_s\, ChgShbChg + v_pShb(Ch^2g + Sh^2g)|$$

where p is the density of soft tissue. Here, $v_p$ and $v_s$ are determined directly by measurement of the first and second critical angles. As $C_{11}$, $C_{12}$, and $C_{13}$ can be expressed in terms of p' (equations H.4, H.7, and H.8) the equation H.9 can be solved for p':

$$\frac{2v_s\, ChgShbChb + v_pShb(Ch^2g + Sh^2g)}{2ShgChgShbChb\left[\frac{C_{13}}{\rho'}\cos^2 \xi + \frac{C_{12}}{\rho'}\sin^2 \xi - \frac{C_{11}}{\rho'}\right] + (Ch^2g + Sh^2g)\left[-\frac{C_{11}}{\rho'}Sh^2b\left(\frac{C_{13}}{\rho'}\cos^2 \xi + \frac{C_{12}}{\rho'}\sin \xi\right)\right]}$$

p' in turn can be used to determine the five elasticity constants (equations H.4–H.8). Furthermore, the third critical angle $\phi_3$ can be used to give additional constraints on the constants. The third critical angle $\phi_3$, like the second critical angle, is less easily measured than the first critical angle, due to the fact that it appears at very large angles.

To summarize, the measurement of the three critical angles ($\phi_1$, $\phi_2$, $\phi_3$) can be utilized to determine density and constants of elasticity. Any number of schemes using at least three planes of scattering can measure the full matrix of elasticity under the assumption of hexagonal symmetry. Furthermore, such a measurement allows optimization using the additional constraints arising naturally from the measurement of the angles.

What is claimed is:

1. An apparatus for investigating the mechanical properties of bone, comprising:
   means for mounting a bone;
   at least one ultrasound transducer positioned for transmitting an ultrasound wave (I) towards the surface of the bone;
   at least one ultrasound transducer positioned for receiving ultrasound waves (R) reflected by the bone surface;
   means for varying the angle of incidence ($\phi$) of the transmitted ultrasound wave (I) towards the bone surface;
   means responsive to emitted ultrasound waves for determining the alignment of said bone surface with respect to said transmitting and receiving transducers; and
   signal analyzer means coupled to at least one of said at least one receiving transducer and said varying means, and also coupled to said alignment determining means, for determining the one or more critical angles at which the amplitude of the reflected ultrasound wave is an extrema.

2. The apparatus according to claim 1, said varying means comprising a stepper mechanism coupled to the transducers for simultaneously moving and positioning the transmitting and receiving transducers in a plane of motion about the bone.

3. The apparatus according to claim 1, wherein said at least one transmitting ultrasound transducer and said at least one receiving ultrasound transducer are comprised in an array of ultrasound transducers spaced about the bone, at least one of the transducer in said array being operable as a transmitting transducer and at least one of the transducer in said array being operable as a receiving transducer.

4. The apparatus according to claim 3, the varying means including a switching circuit for selectably operating at least one transducer in said array as said at least on transmitting ultrasound transducer positioned at different angles relative to the bone to selectably transmit ultrasound waves at varying angles of incidence.

5. The apparatus according to claim 4, the switching circuit being operable for selectably operating at least one transducer as a receiving transducer positioned at and about an angle of reflection approximately equal to the angle of incidence of the transmitting transducer in use.

6. The apparatus according to claim 1, the mounting means including a water tank for receiving a bone.

7. The apparatus according to claim 1, the mounting means including a bag containing water, other liquids or gel to act as a coupling medium between transducers and bone, adjacent the transmitting and receiving transducers and positionable adjacent the bone of a patient.

8. The apparatus according to claim 1, said signal analyzer means being operable for using a first critical angle ($\phi_1$), for measuring the velocity of a pressure wave (Vp) in the bone, for using a second critical angle ($\phi_2$) for measuring the velocity of a shear wave (Vs) in the bone, for using both the first and second critical angles ($\phi_1$ and $\phi_2$, respectively for measuring Young's modulus of elasticity (E), and for using the first and second critical angles ($\phi_1$ and $\phi_2$, respectively) for measuring Poisson's modulus ($p$).

9. The apparatus according to claim 8, wherein the signal analyzer means measures the pressure wave velocity ($v_p$) using the formula:

$$v_p = \frac{C}{\sin \phi_1}$$

wherein C is the velocity of the transmitted ultrasound wave (I) in the medium separating the transmitting transducer and bone.

10. The apparatus according to claim 8, in which the first critical angle ($\phi_1$) is obtained when the angle of refraction of the pressure wave in the bone (B) resulting from the transmitted wave is about $\pi/2$.

11. The apparatus according to claim 8, the signal analyzer means being operable for measuring the bone density (p') using the velocity of the pressure wave ($v_p$) in the bone.

12. The apparatus according to claim 1, the mounting means including a bag containing water, other liquids or gel to act as a coupling medium between transducers and tissue, adjacent the transmitting and receiving transducers and positionable adjacent the bone of a patient.

13. A method of investigating the mechanical properties of bone comprising the steps of:
   transmitting an ultrasound wave (I) to impinge the bone surface at an angle of incidence ($\phi$);
   receiving the ultrasound wave (R) reflected from the bone surface;
   determining, by means of emitted ultrasound waves, the alignment of said bone surface with respect to said transmitted ultrasound wave (I) and said reflected ultrasound wave (R);
   varying the angle of incidence ($\phi$) in the range of 0–90° while transmitting and receiving; and
   determining a first critical angle ($\phi_1$) in which the amplitude of the reflected waves (R) is an extrema.

14. The method according to claim 13, wherein the first critical angle ($\phi$) occurs when the angle (B) of the pressure wave ($T_p$) in the bone is at an angle of refraction of about $\pi/2$.

15. The method according to claim 13, including the step of approximately the velocity of the pressure wave ($v_p$) in the bone using said first critical angle ($\phi_1$).

16. The method according to claim 15, wherein the approximating step includes the substep of computing said pressure wave velocity ($v_p$) using the relationship;

$$v_p = \frac{C}{\sin \phi_1}$$

where C is the velocity of the transmitted ultrasound wave (I) in the medium adjacent the bone.

17. The method according to claim 16, including the step of approximating the density of the bone (p') using the pressure wave velocity ($v_p$).

18. The method according to claim 17, wherein the density approximating step includes the substep of computing the bone density (p') using the relationship:

$$p' = \frac{1}{v_p} pc \frac{1 + \frac{R}{I_o}}{1 - \frac{R}{I_o}}$$

where p is the density of the medium adjacent the bone, and c is the velocity of the transmitted ultrasound wave (I) in the medium adjacent the bone, and $R/I_o$ is the ratio of reflected to incident amplitude at small angles.

19. The method according to claim 18, including the steps of approximating the velocity of the shear wave ($v_s$) in the bone using a second critical angle ($\phi_2$) in which the amplitude of the reflected waves (R) is another maxima which is followed by a deep minimum or an inflection point following a deep minimum and preceding a maximum, and approximating Young's modulus of elasticity (E) using the relationship:

$$\frac{E}{p} = v_s^2 \frac{3v_p^2 - 4v_s^2}{v_p^2 - v_s^2}$$

where p is the density of the medium adjacent the bone.

20. The method according to claim 18, including the step of approximately the velocity of the shear wave ($v_s$) in the bone using a second critical angle ($\phi_2$) in which the amplitude of the reflected waves (R) is another maxima which is followed by a deep minimum or an inflection point following a deep minimum and preceding a maximum, and approximating Poisson's modulus ($\sigma$) using the relationship:

$$\sigma = \frac{v_p^2 - 2v_s^2}{2(v_p^2 - v_s^2}$$

21. The method according to claim 13, including the step of determining a second critical angle ($\phi_2$) in which the amplitude of the reflected waves (R) is a second maxima.

22. The method according to claim 21, wherein the second critical angle ($\phi_2$) occurs when the angle ($\gamma$) of the shear wave ($T_s$) in the bone is at an angle of refraction of about $\pi/2$.

23. The method according to claim 21, including the step of approximating the velocity of the shear wave ($v_s$) in the bone using said second critical angle ($\phi_2$).

24. The method according to claim 23, wherein the approximating step includes the substep of computing said pressure wave velocity ($v_s$) using the relationship:

$$v_s = \frac{C}{\sin \phi_2}$$

where C is the velocity of the transmitted ultrasound wave (I) in the medium adjacent the bone.

25. The method according to claim 21, wherein the first critical angle ($\phi_1$) occurs at about the first maxima obtained as the angle of incidence ($\phi$) is increased in the range 0°–90° and the second critical angle ($\phi_2$) occurs at a second maxima after said first maxima.

26. The method according to claim 25, including the step of determining a third critical angle ($\phi_3$), which occurs after the first critical angle ($\phi_1$), and in which the amplitude of the reflected waves (R) changes sign and shows as a deep minima approaching 0.

27. The method according to claim 26, including the step of determining the five independent elements of the matrix of elasticity ($C_{11}$, $C_{12}$, $C_{13}$, $C_{33}$, $C_{44}$) using the three critical angles ($\phi_1$, $\phi_2$, $\phi_3$) assuming the bone is generally transversely (hexagonally) symmetrical.

28. The method according to claim 26, including the step of defining the nine independent elements of the matrix of elasticity ($C_{11}$, $C_{22}$, $C_{33}$, $C_{44}$, $C_{55}$, $C_{66}$, $C_{12}$, $C_{13}$, $C_{23}$) using the three critical angle ($\phi_1$, $\phi_2$, $\phi_3$) assuming the bone is generally orthorhombic.

29. The method according to claim 13, including the step of determining the composition of the bone.

30. The method according to claim 29, the composition determining step comprising determining whether the bone is isotropic, transversely isotropic, or more complex.

31. An apparatus for investigating the mechanical properties of a material comprising:
   means for transmitting an ultrasound wave (I) at the surface of the solid;
   means for receiving an ultrasound wave positioned for detecting the ultrasound wave (R) reflected by the material;
   means for varying the angle of the incidence ($\phi$) of the transmitted ultrasound wave (I) relative to the material;
   means responsive to emitted ultrasound waves for determining the alignment of said solid surface with respect to said ultrasound transmitting and receiving means; and
   signal analyzer means coupled to the receiving means for determining when the amplitude of the reflected wave (R) is an extrema,
      coupled to the varying means to determine the angle of incidence ($\phi$) of the transmitted ultrasound wave (I) relative to the solid, and also coupled to said alignment determining means,
      operable to correlate said extrema of the reflected amplitude to said angle of incidence ($\phi$) to determine one or more critical angles corresponding to said extrema.

32. The apparatus according to claim 31, wherein the varying means controls the angle of incidence increasing in the range 0° to 90° and the first maxima encountered corresponds to a first critical angle ($\phi_1$).

33. The apparatus according to claim 31, wherein said transmitting means and receiving means each comprises an ultrasound transducer.

34. The apparatus according to claim 33, wherein said varying means comprises a stepper mechanism to step the transmitting and receiving transducers simultaneously through increasing angles of incidence ($\phi$) and angles of reflection, respectively, where the angle of reflection approximates the angle of incidence ($\phi$).

35. The apparatus according to claim 31, including an array of ultrasound transducers wherein one or more transducers are selectably operable as said transmitting means and one or more transducers are selectably operable as said receiving means.

36. The apparatus according to claim 34, wherein said varying means is operable for incrementally transmitting the wave (I) at angles of incidence increasing in the range 0°–90°.

37. The apparatus according to claim 31, including a fluid medium separating the transmitting means and receiving means from the material.

38. The apparatus according to claim 31, said signal analyzer means being operable for approximating the velocity of the pressure wave ($v_p$) in the material based on a first critical angle ($\phi_1$) corresponding to a first maxima encountered as the angle of incidence ($\phi$) increases in the range of 0°–90°.

39. The apparatus according to claim 38, said signal analyzer means being operable for approximating the velocity of the shear wave ($v_s$) in the material based on a second critical angle ($\phi_2$) corresponding either to a second maxima followed by a deep minimum or to an inflection point following a deep minimum and encountered after the first maxima as the angle of incidence ($\phi$) increases in the range of 0°–90°.

40. The apparatus according to claim 39, said signal analyzer means being operable to calculate the approximate density and modulus of elasticity based on said pressure and shear velocities ($v_p$, $v_s$).

41. A method of investigating the mechanical properties of a material comprising the steps of:
   directing ultrasound waves (I) towards the surface of the solid at an angle of incidence ($\phi$);
   varying the angle of incidence ($\phi$) of the directed waves (I) relative to the surface of the material;
   receiving reflected ultrasound waves (R) from the surface of the material as the angle of incidence ($\phi$) is varied;
   determining, by means of emitted ultrasound waves, the alignment of said solid surface with respect to said directed ultrasound waves (I) and said reflected ultrasound waves (R); and
   determining the one or more critical angles of incidence that correspond to extrema values of the amplitude of the reflected ultrasound waves (R).

42. The method according to claim 41, including the step of approximating the velocity of the pressure wave ($v_p$) in the material resulting from the directed waves (I) using a first critical angle ($\phi_1$).

43. The method according to claim 42, the first critical angle ($\phi_1$) for approximating the velocity of the pressure wave ($v_p$) occurring about when the angle (B) of the pressure wave in the material ($T_p$) relative to the normal of the surface of the material is about $\pi/2$, 44. The method according to claim 41, wherein the pressure wave velocity ($v_p$) is approximated using the relationship:

$$v_p = \frac{c}{\sin \phi_1}$$

where ($\phi_1$) is said first critical angle and c is the velocity of the directed wave (I) prior to the surface.

45. The method according to claim 41, including the step of approximating the density of the material (p') using a critical angle.

46. The method according to claim 45, the density approximating step including the substeps of approximating the velocity of the pressure wave ($v_p$) in the material and approximating the density (p') using the relationship:

$$p' = \frac{1}{v_p} pc \frac{1 + \frac{R}{I_o}}{1 - \frac{R}{I_o}}$$

where p is the density of the medium through which the directed waves (I) travel prior to the material, c is the velocity of the directed wave (I) through said medium, $v_p$ is determined using the relationship $$v_p = \frac{c}{\sin \phi_1},$$

and the reflected amplitude is measured at small values of $\phi$.

47. The method according to claim 41, including the step of approximating Young's modulus of elasticity (E) using critical angles ($\phi_1$, $\phi_2$).

48. The method according to claim 47, wherein the pressure wave velocity ($v_p$) is approximated using the first critical angle ($\phi_1$) and the shear wave velocity ($v_s$) is approximated using the second critical angle ($\phi_2$), wherein Young's modulus is approximated by the relationship:

$$\frac{E}{p} = v_s^2 \frac{3v_p^2 - 4v_s^2}{v_p^2 - v_s^2}$$

where p is the density of the medium through which the direct waves (I) travel prior to the material.

49. The method according to claim 47, wherein the pressure wave velocity ($v_p$) is approximated using the first critical angle ($\phi_1$) and the shear wave velocity ($v_s$) is approximated using the second critical angle ($\phi_2$), wherein Poisson's modulus ($\sigma$) is approximated by the relationship:

$$\sigma = \frac{v_p^2 - 2v_s^2}{2 v_p^2 - v_s^2}$$

50. The method according to claim 41, including the step of approximating Poisson's modulus (o) using critical angles ($\phi_1$, $\phi_2$).

51. The method according to claim 41, including the step of approximating the velocity of the shear wave ($v_s$) in the material resulting from the directed waves (I) using a second critical angle ($\phi_2$).

52. The method according to claim 51, wherein the shear wave velocity ($v_s$) is approximated using the relationship $$v_s = \frac{c}{\sin \phi_2}$$

where c is the velocity of the directed wave (I) in the medium prior to the surface.

53. The method according to claim 41, wherein a first critical angle ($\phi_1$) occurs at the first maxima occurring as the angle of incidence ($\phi$) increases in the range 0°–90° and a second critical angle ($\phi_2$) occurs at a next maxima or inflection point following the first maxima.

54. The method according to claim 53, wherein a third critical angle ($\phi_3$) occurs as a minima after said first ($\phi_1$) critical angle as the amplitude of the reflected ultrasound waves (R) vanishes (becomes zero).

55. The method according to claim 54, including the step of approximating the density of the material using the three critical angles ($\phi_1$, $\phi_2$, $\phi_3$).

56. The method according to claim 54, wherein the material is human bone having a generally transverse (hexagonal) symmetry, including the step of approximating the constants of elasticity of the bone using the three critical angles ($\phi_1$, $\phi_2$, $\phi_3$) measured in at least three planes of scattering.

57. The method according to claim 54, wherein the material is human bone having a generally orthorhombic symmetry, including the step of approximating the constants of elasticity matrix of the bone using the three critical angles ($\phi_1$, $\phi_2$, $\phi_3$) measured in at least three planes of scattering.

* * * * *

UNITED STATES PATENT AND TRADEMARK OFFICE
CERTIFICATE OF CORRECTION

PATENT NO. : 5,038,787
DATED : August 13, 1991
INVENTOR(S) : Pietro P. Antich, et al.

It is certified that error appears in the above-identified patent and that said Letters Patent is hereby corrected as shown below:

At column 5, line 32, a period should be inserted before the word "Preferably".

At column 14, line 25, after the word "axis" insert --. Fig. 8--.

Figure 9:
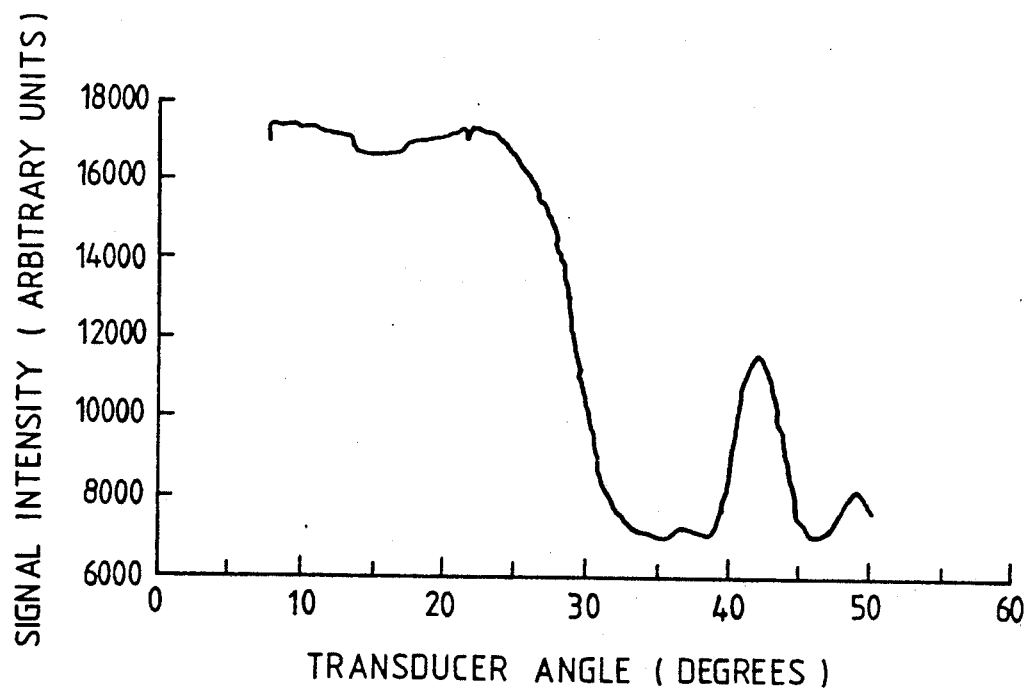
FIG. 9 is a graph illustrating signal intensity as the function of transducer angle along the longer axis of polished, preserved bone.

At column 14, line 29, after "at 25°.", insert --Fig. 9 illustrates the results that were obtained when the bone was examined along its longer axis, rather than the shorter axis shown in Fig. 8.--

At column 18, line 56, the colon which appears after "Fig. 11" should instead be a period.

At column 19, line 25, after the phrase "(direction of the scan)" insert a period.

At column 20, line 42, "t he" should instead read --the--.

In column 21, line 36, after the phrase "at least one of the", the word "transducer" should instead --transducers--.

UNITED STATES PATENT AND TRADEMARK OFFICE
CERTIFICATE OF CORRECTION

PATENT NO.    : 5,038,787
DATED         : August 13, 1991
INVENTOR(S)   : Pietro P. Antich, et al.

It is certified that error appears in the above-identified patent and that said Letters Patent is hereby corrected as shown below:

At column 21, line 38, in the phrase "the transducer in said array being operable", the word "transducer" should instead read --transducers--.

In column 22, line 49, the semicolon at the end of the line should instead be a colon.

In column 23, line 19, the word "approximately" should instead read --approximating--.

At column 23, line 29, a closing parentheses should be added at the lower right of the equation.

At column 24, line 53, "34" should instead read --35--.

In column 25, line 35, "41" should instead read --42--.

Signed and Sealed this

Fifth Day of January, 1993

*Attest:*

DOUGLAS B. COMER

*Attesting Officer*      Acting Commissioner of Patents and Trademarks